United States Patent
Sugiyama et al.

(10) Patent No.: US 7,378,384 B2
(45) Date of Patent: May 27, 2008

(54) WT1 SUBSTITUTION PEPTIDES

(75) Inventors: Haruo Sugiyama, Minoo (JP);
Masashi Gotoh, Takatsuki (JP); Hideo Takasu, Nishinomiya (JP); Fumio Samizo, Suita (JP); Naoto Kusunose, Aioi (JP); Masashi Nakatsuka, Mishima-gun (JP)

(73) Assignees: International Institute of Cancer Immunology, Inc., Suita-shi (JP); Chugai Seiyaku Kabushiki Kaisha, Tokyo-to (JP); Dainippon Sumitomo Pharma Co., Ltd., Osaka-shi (JP)

(*) Notice: Subject to any disclaimer, the term of this patent is extended or adjusted under 35 U.S.C. 154(b) by 178 days.

(21) Appl. No.: 10/528,360

(22) PCT Filed: Sep. 19, 2003

(86) PCT No.: PCT/JP03/11974

§ 371 (c)(1),
(2), (4) Date: Mar. 18, 2005

(87) PCT Pub. No.: WO2004/026897

PCT Pub. Date: Apr. 1, 2004

(65) Prior Publication Data

US 2006/0205667 A1    Sep. 14, 2006

(30) Foreign Application Priority Data

Sep. 20, 2002   (JP)   ............... 2002-275264

(51) Int. Cl.
*A61K 38/02*    (2006.01)
*A61K 38/08*    (2006.01)

(52) U.S. Cl. .......................................... 514/2; 514/15
(58) Field of Classification Search .................... None
See application file for complete search history.

(56) References Cited

U.S. PATENT DOCUMENTS

| | | |
|---|---|---|
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2005/0266014 A1 | 12/2005 | Sugiyama et al. |

FOREIGN PATENT DOCUMENTS

| | | |
|---|---|---|
| EP | 1 103 564 A1 | 5/2001 |
| EP | 1 371 664 A1 | 12/2003 |
| EP | 1 447 092 A1 | 8/2004 |
| WO | 00 18795 | 4/2000 |
| WO | WO-02/079253 A | 10/2002 |
| WO | WO-03/028758 A | 4/2003 |

OTHER PUBLICATIONS

Gorman C., The hope and the hype, May 1998, Time, v151, p. 37.*
Zips D. et al., New anticancer agents:In vitro and In vivo evaluation, 2005, in vivo, v19, p. 1-9.*
U.S. Appl. No. 10/528,360, filed Mar. 18, 2005, Sugiyama et al.
U.S. Appl. No. 11/322,245, filed Jan. 3, 2006, Sugiyama et al.
Tsuboi et al., Cancer Immunol Immunother., (Dec. 2002), vol. 51, No. 11-12, pp. 614 to 620.
Makita et al., Clin Cancer Res., (Aug. 2002), vol. 8, No. 8, pp. 2626 to 2631.
L. Meadows et al., *Immunity*, vol. 6, 273-281, Mar. 1997.
Y. Kawakami et al., *The Journal of Immunology*, 1998, 161: 6985-6992.
D. J. Kittlesen et al., *The Journal of Immunology*, 1998, 160: 2099-2106.
K. M. Call et al., *Cell*, vol. 60, 509-520, Feb. 9, 1990.
U.S. Appl. No. 09/744,815, filed Jan. 30, 2001, Sugiyama et al.
U.S. Appl. No. 10/517,600, filed Dec. 13, 2004, Sugiyama et al.
U.S. Appl. No. 10/527,692, filed Mar. 11, 2005, Sugiyama.
U.S. Appl. No. 11/196,452, filed Aug. 4, 2005, Sugiyama et al.
U.S. Appl. No. 10/541,821, filed Jul. 11, 2005, Sugiyama et al.
U.S. Appl. No. 10/562,486, filed Dec. 27, 2005, Sugiyama.

* cited by examiner

*Primary Examiner*—Anish Gupta
*Assistant Examiner*—Ronald T Niebauer
(74) *Attorney, Agent, or Firm*—Oblon, Spivak, McClelland, Maier & Neustadt, P.C.

(57) ABSTRACT

Novel substituted type peptides of WT1 wherein the cysteine residue is substituted with a defined amino acid residue, polynucleotides encoding said peptides, cancer vaccines using those peptides or polynucleotides in vivo or in vitro, or the like are provided.

Peptides which comprise an amino acid sequence of the formula: X-Y-Thr-Trp-Asn-Gln-Met-Asn-Leu (SEQ ID NO: 4) wherein X represents Ser, Ala, Abu, Arg, Lys, Orn, Cit, Leu, Phe, or Asn, and Y represents Tyr or Met, and which has an activity to induce CTLs, polynucleotides encoding said peptides, cancer vaccines which comprise those peptides or polynucleotides as an active ingredient, and the like are disclosed.

6 Claims, 9 Drawing Sheets

SEQUENCE LISTING

```
<160> NUMBER OF SEQ ID NOS: 26

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60
```

```
Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
    355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
    435                 440                 445

Leu

<210> SEQ ID NO 2
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 2

Cys Met Thr Trp Asn Gln Met Asn Leu
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Cys Tyr Thr Trp Asn Gln Met Asn Leu
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Ser, Ala, Abu, Arg, Lys, Orn, Cit, Leu,
      Phe or Asn
<220> FEATURE:
<221> NAME/KEY: Misc_Feature
<222> LOCATION: (2)..(2)
<223> OTHER INFORMATION: Xaa is Tyr or Met

<400> SEQUENCE: 4

Xaa Xaa Thr Trp Asn Gln Met Asn Leu
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ser Tyr Thr Trp Asn Gln Met Asn Leu
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Ala Tyr Thr Trp Asn Gln Met Asn Leu
  1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Abu

<400> SEQUENCE: 7

Xaa Tyr Thr Trp Asn Gln Met Asn Leu
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Arg Tyr Thr Trp Asn Gln Met Asn Leu
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Lys Tyr Thr Trp Asn Gln Met Asn Leu
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Orn

<400> SEQUENCE: 10

Xaa Tyr Thr Trp Asn Gln Met Asn Leu
  1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Cit

<400> SEQUENCE: 11

Xaa Tyr Thr Trp Asn Gln Met Asn Leu
  1               5

<210> SEQ ID NO 12
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Leu Tyr Thr Trp Asn Gln Met Asn Leu
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Phe Tyr Thr Trp Asn Gln Met Asn Leu
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Asn Tyr Thr Trp Asn Gln Met Asn Leu
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Ser Met Thr Trp Asn Gln Met Asn Leu
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ala Met Thr Trp Asn Gln Met Asn Leu
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
```

```
<223> OTHER INFORMATION: Xaa is Abu

<400> SEQUENCE: 17

Xaa Met Thr Trp Asn Gln Met Asn Leu
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Arg Met Thr Trp Asn Gln Met Asn Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Lys Met Thr Trp Asn Gln Met Asn Leu
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Orn

<400> SEQUENCE: 20

Xaa Met Thr Trp Asn Gln Met Asn Leu
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Misc_Feature
<222> LOCATION: (1)..(1)
<223> OTHER INFORMATION: Xaa is Cit

<400> SEQUENCE: 21

Xaa Met Thr Trp Asn Gln Met Asn Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
```

-continued

<400> SEQUENCE: 22

Leu Met Thr Trp Asn Gln Met Asn Leu
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Phe Met Thr Trp Asn Gln Met Asn Leu
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Asn Met Thr Trp Asn Gln Met Asn Leu
 1               5

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Phe Asn Asn Phe Thr Val Ser Phe Trp Leu Arg Val Pro Lys Val Ser
 1               5                  10                  15

Ala Ser His Leu Glu
             20

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Ala Gln Tyr Ile Lys Ala Asn Ser Lys Phe Ile Gly Ile Thr Glu Leu
 1               5                  10                  15

WT1 SUBSTITUTION PEPTIDES

TECHNICAL FIELD

The present invention relates to novel substituted type peptides of WT1. Specifically, the invention relates to substituted type peptides of WT1 wherein the cysteine residue is substituted with a defined amino acid residue, use of them as cancer vaccines, and the like.

BACKGROUND ART

A cysteine residue comprised in a peptide may be oxidized in a solution to produce a disulfide bond. A peptide comprising a reduced cysteine residue and a peptide comprising an oxidized one are drastically different each other in the structure, and, in the course of the use of them as cancer vaccines, CTLs specific for one of the peptides are not always reactive to the other (*Immunity* 1997; 6: 273-281). Thus, when a cancer antigen peptide comprising a cysteine residue is designed as a pharmaceutical composition of a cancer vaccine, it would be believed to provide an advantage that a peptide wherein a cysteine residue comprised in the cancer antigen peptide is substituted with another amino acid residue is developed in stead of the antigen peptide. However, a peptide wherein a cysteine residue is substituted with another amino acid residue does not necessarily function as a cancer antigen peptide, and such substituted type peptides provide largely different efficacy (*J. Immunol.*, 1998; 161:6985-6992, *J. Immunol.*, 1998; 160:2099-2106).

WT1$_{235-243}$ (Cys-Met-Thr-Trp-Asn-Gln-Met-Asn-Leu; SEQ ID NO: 2), that is a peptide spanning in positions 235 to 243 of the cancer antigen protein, WT1 (SEQ ID NO: 1, *Cell.*, 60:509, 1990), is a cancer antigen peptide having an activity to induce CTLs in HLA-A24-restricted manner (*Clin. Cancer. Res.* 8: 2626, 2002, and WO 00/06602). The altered peptide (Cys-Tyr-Thr-Trp-Asn-Gln-Met-Asn-Leu; SEQ ID NO: 3, hereinafter it may be referred to as WT1$_{235-243}$ (2M→Y)) wherein the methionine at position 2 of WT1$_{235-243}$ is altered to tyrosine has a higher binding activity to the HLA-A24 antigen than the natural type peptide (WO 02/079253, the international publication date: Oct. 10, 2002). The natural type peptide, WT1$_{235-243}$, and the altered peptide, WT1$_{235-243}$ (2M→Y), are both expected to become an active agent for cancer immunotherapy.

DISCLOSURE OF THE INVENTION

The present invention aims to provide novel substituted type peptides of WT1 wherein the cysteine residue is substituted with a defined amino acid residue, use of them as cancer vaccines, and the like.

The inventors of the present application conducted the substitution of the cysteine residue at position 1 in WT1$_{235-243}$ and WT1$_{235-243}$ (2M→Y) (hereinafter, the peptide may be also referred to as "non-substituted type peptide") with various amino acid residues to prepare diverse substituted type peptides, and examined for their in vivo immunogenicity using HLA-A2402/K$^b$ transgenic mice (WO 02/47474, hereinafter, they may be also referred to as "HLA-A24-expressing transgenic mice"). As the results, the present inventors surprisingly found that a substituted type peptide wherein the cysteine residue is substituted with serine residue (Ser), alanine residue (Ala), arginine residue (Arg), lysine residue (Lys), leucine residue (Leu), phenylalanine residue (Phe), or asparagine residue (Asn), all of which are different from a cysteine residue in structure and property, has an activity to induce CTLs (an immunogenicity) equivalent to the non-substituted type peptide. Even more surprisingly, the present inventors found that a substituted type peptide wherein the cysteine residue at position 1 is substituted with 2-aminobutyric acid residue (α-aminobutyric acid residue, Abu), ornithine residue (Orn), or citrulline residue (Cit), all of which are not a proteinogenic amino acid naturally occurring (an unusual amino acid residue), also has an activity to induce CTLs (an immunogenicity) equivalent to the non-substituted type peptide. On the basis of those findings, the inventors hold the conviction that the substituted type peptides as shown above should be available as cancer vaccines in various forms. The substituted type peptides do not produce a disulfide bond since they comprise no cysteine residue, and thus they have advantages such as easy standardization of medical products. The present invention has been completed on the basis of the findings as described above.

Thus, the present invention relates to:

(I) a peptide which comprises or consists of an amino acid sequence of the formula:

X-Y-Thr-Trp-Asn-Gln-Met-Asn-Leu
(SEQ ID NO: 4)

wherein X represents Ser, Ala, Abu, Arg, Lys, Orn, Cit, Leu, Phe, or Asn, and Y represents Tyr or Met, and which has an activity to induce CTLs; preferably, the peptide according to above (I) which comprises or consists of any one of the amino acid sequences selected from a group consisting of:

Ser-Thr-Trp-Asn-Gln-Met-Asn-Leu (SEQ ID NO: 4)

Ala-Tyr-Thr-Trp-Asn-Gln-Met-Asn-Leu (SEQ ID NO: 6),

Abu-Tyr-Thr-Trp-Asn-Gln-Met-Asn-Leu (SEQ ID NO: 7),

Arg-Tyr-Thr-Trp-Asn-Gln-Met-Asn-Leu (SEQ ID NO: 8),

Lys-Tyr-Thr-Trp-Asn-Gln-Met-Asn-Leu (SEQ ID NO: 9),

Orn-Tyr-Thr-Trp-Asn-Gln-Met-Asn-Leu (SEQ ID NO: 10),

Cit-Tyr-Thr-Trp-Asn-Gln-Met-Asn-Leu (SEQ ID NO: 11),

Leu-Tyr-Thr-Trp-Asn-Gln-Met-Asn-Leu (SEQ ID NO: 12),

Phe-Tyr-Thr-Trp-Asn-Gln-Met-Asn-Leu (SEQ ID NO: 13),

Asn-Tyr-Thr-Trp-Asn-Gln-Met-Asn-Leu (SEQ ID NO: 14),

Ser-Met-Thr-Trp-Asn-Gln-Met-Asn-Leu (SEQ ID NO: 15), and

Ala-Met-Thr-Trp-Asn-Gln-Met-Asn-Leu (SEQ ID NO: 16), as well as a process for preparing those peptides;

(II) a polynucleotide which encodes the peptide according to above (I), an expression vector which contains the polynucleotide, and a cell which comprises the expression vector;

(III) an antibody which specifically binds to a peptide according to above (I);

(IV) an antigen-presenting cell on which a complex between a cancer antigen peptide derived from the peptide according to above (I) and an HLA-A24 antigen is presented;

(V) a CTL which recognizes a complex between a cancer antigen peptide derived from the peptide according to above (I) and an HLA-A24 antigen;

(VI) a pharmaceutical composition which comprises the peptide according to above (I), the polynucleotide according to above (II), the expression vector, the cell, the antigen-presenting cell according to above (IV), or the CTL according to above (V), together with a pharmaceutically acceptable carrier, and the pharmaceutical composition used as a cancer vaccine;

(VII) use of the peptide according to above (I), the polynucleotide according to above (II), the expression vector, the cell, the antigen-presenting cell according to above (IV), or the CTL according to above (V) in the manufacture of a cancer vaccine;

(VIII) a method for treatment or prevention of a cancer, which comprises administering a therapeutically or prophylactically effective amount of the peptide according to above (I), the polynucleotide according to above (II), the expression vector, the cell, the antigen-presenting cell according to above (IV), or the CTL according to above (V), to a cancer patient in need who is positive for an HLA-A24, and positive for WT1.

BEST MODE FOR CARRYING OUT THE INVENTION

Figure 1:
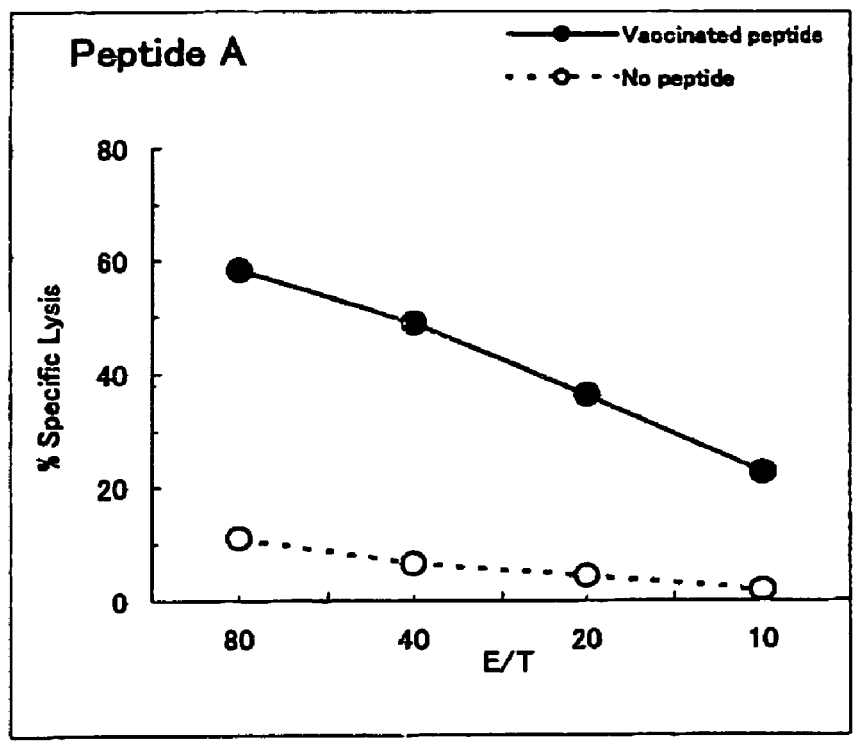
FIG. 1 is a graph showing that specific CTLs were induced when an HLA-A24-expressing transgenic mouse was immunized with peptide A wherein the amino acid at position 2 in the antigen peptide derived from human WT1 ($WT1_{235-243}$) is substituted with a tyrosine residue. In the figure, the vertical axis shows cytotoxic activity (% Specific Lysis), and the horizontal axis shows E/T ratio. Also, in the figure, the solid circle shows the results obtained using target cells pulsed with peptide A, and the open circle shows the results obtained using cells not pulsed with any peptide.
Figure 2:
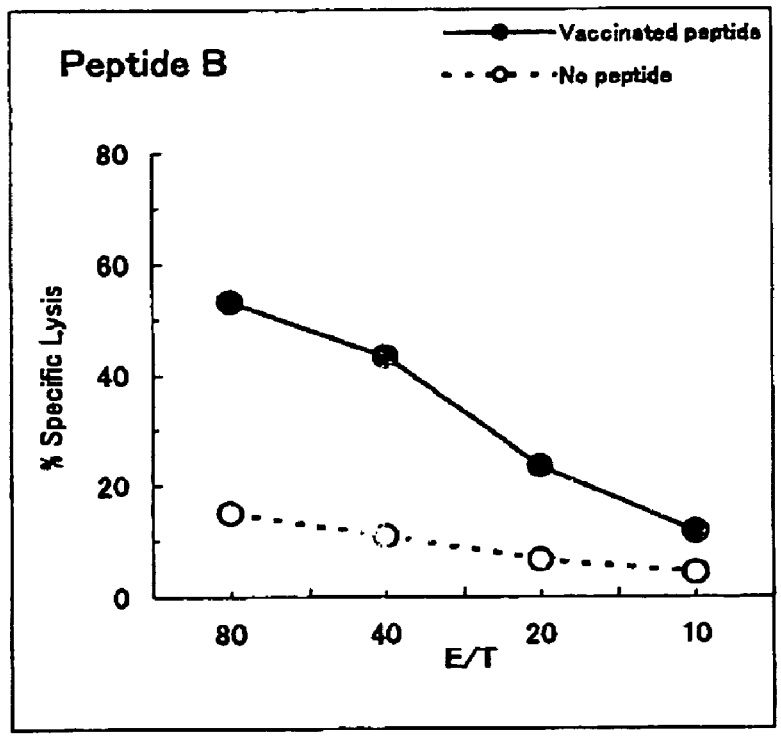
FIG. 2 is a graph showing that specific CTLs were induced when an HLA-A24-expressing transgenic mouse was immunized with peptide B wherein the cysteine residue at position 1 in peptide A is substituted with a serine residue. In the figure, the vertical axis shows cytotoxic activity (% Specific Lysis), and the horizontal axis shows E/T ratio. Also, in the figure, the solid circle shows the results obtained using target cells pulsed with peptide B, and the open circle shows the results obtained using cells not pulsed with any peptide.
Figure 3:
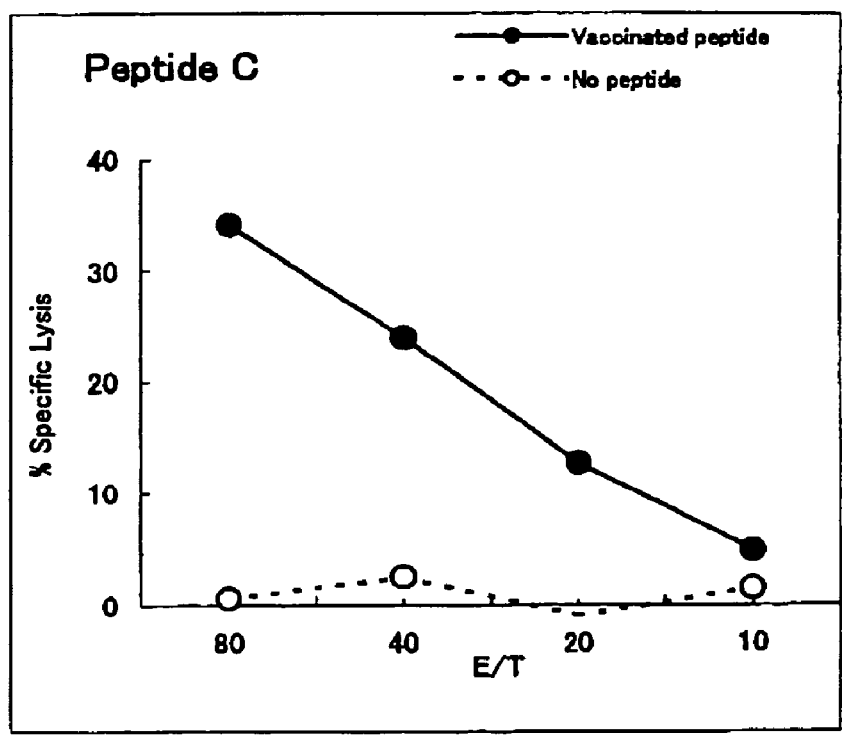
FIG. 3 is a graph showing that specific CTLs were induced when an HLA-A24-expressing transgenic mouse was immunized with peptide C wherein the cysteine residue at position 1 in peptide A is substituted with an alanine residue. In the figure, the vertical axis shows cytotoxic activity (% Specific Lysis), and the horizontal axis shows E/T ratio. Also, in the figure, the solid circle shows the results obtained using target cells pulsed with peptide C, and the open circle shows the results obtained using cells not pulsed with any peptide.
Figure 4:
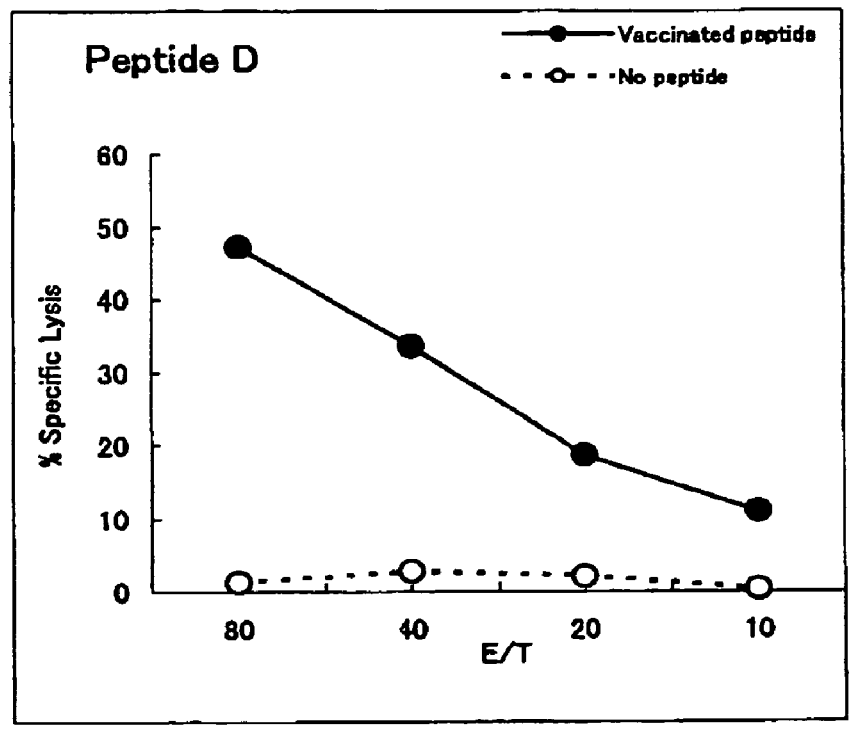
FIG. 4 is a graph showing that specific CTLs were induced when an HLA-A24-expressing transgenic mouse was immunized with peptide D wherein the cysteine residue at position 1 in peptide A is substituted with a 2-aminobutyric acid residue. In the figure, the vertical axis shows cytotoxic activity (% Specific Lysis), and the horizontal axis shows E/T ratio. Also, in the figure, the solid circle shows the results obtained using target cells pulsed with peptide D, and the open circle shows the results obtained using cells not pulsed with any peptide.
Figure 5:
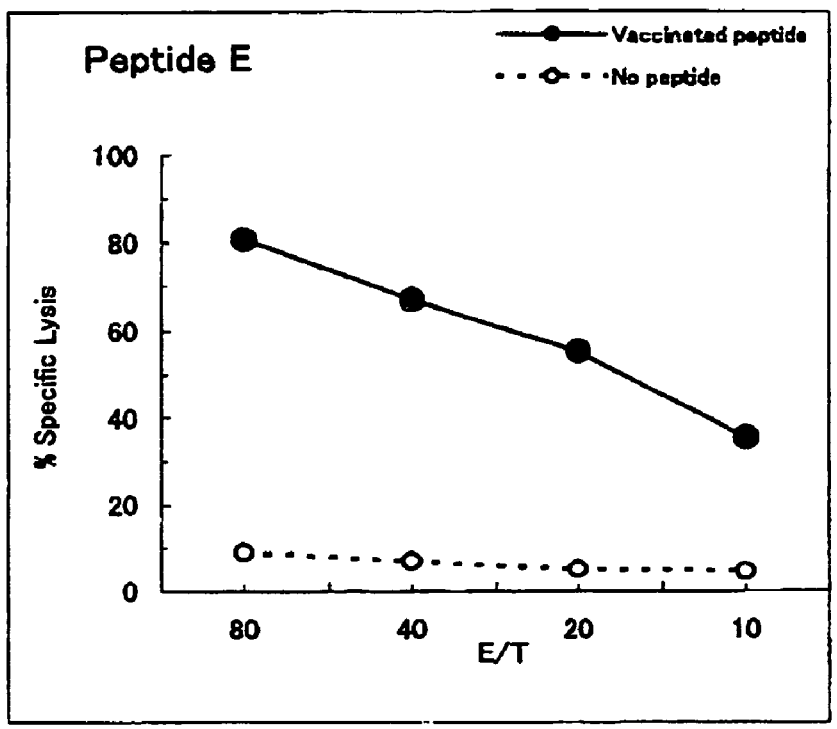
FIG. 5 is a graph showing that specific CTLs were induced when an HLA-A24-expressing transgenic mouse was immunized with peptide E wherein the cysteine residue at position 1 in peptide A is substituted with an arginine residue. In the figure, the vertical axis shows cytotoxic activity (% Specific Lysis), and the horizontal axis shows E/T ratio. Also, in the figure, the solid circle shows the results obtained using target cells pulsed with peptide E, and the open circle shows the results obtained using cells not pulsed with any peptide.
Figure 6:
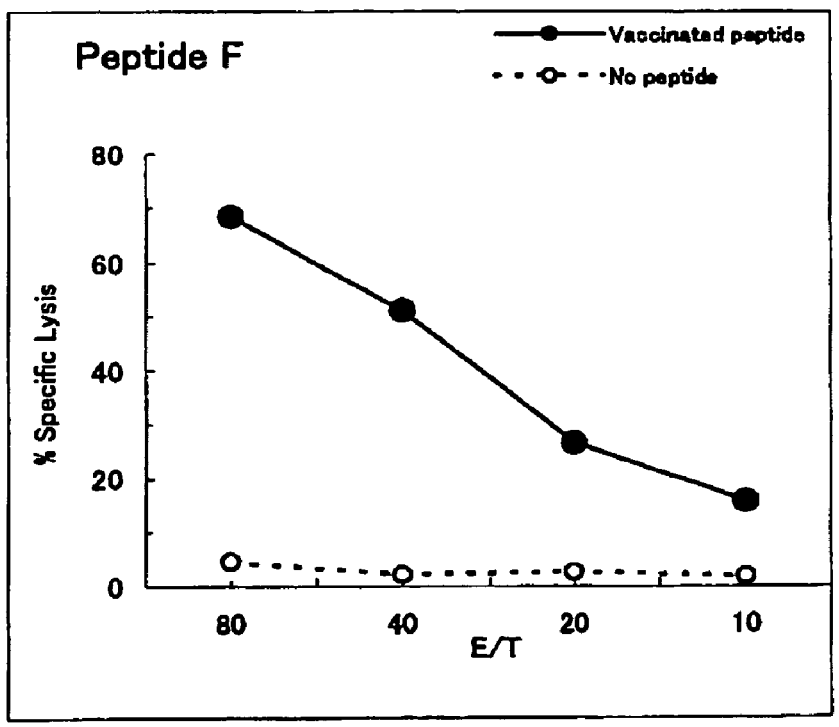
FIG. 6 is a graph showing that specific CTLs were induced when an HLA-A24-expressing transgenic mouse was immunized with peptide F wherein the cysteine residue at position 1 in peptide A is substituted with a lysine residue. In the figure, the vertical axis shows cytotoxic activity (% Specific Lysis), and the horizontal axis shows E/T ratio. Also, in the figure, the solid circle shows the results obtained using target cells pulsed with peptide F, and the open circle shows the results obtained using cells not pulsed with any peptide.
Figure 7:
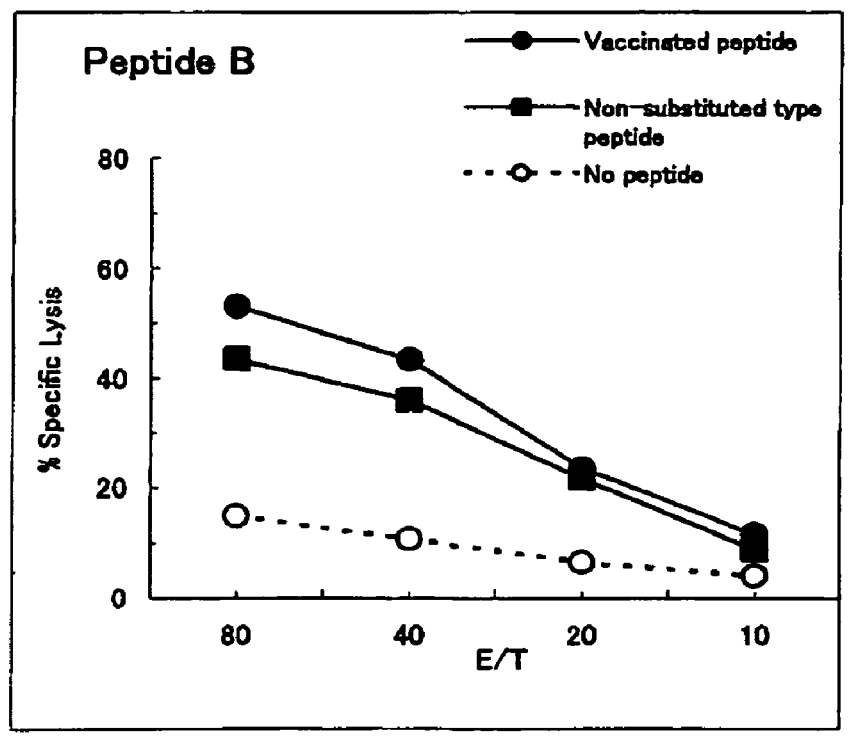
FIG. 7 is a graph showing the results of the test for cross-reactivity of the effector cells induced by the substituted type peptide, peptide B to the non-substituted type peptide, peptide A. In the figure, the vertical axis shows CTL-inducing activity (% Specific Lysis), and the horizontal axis shows E/T ratio. Also, in the figure, the solid circle shows the results obtained using target cells pulsed with peptide B, the solid square shows the results obtained using target cells pulsed with peptide A, and the open circle shows the results obtained using cells not pulsed with any peptide.
Figure 8:
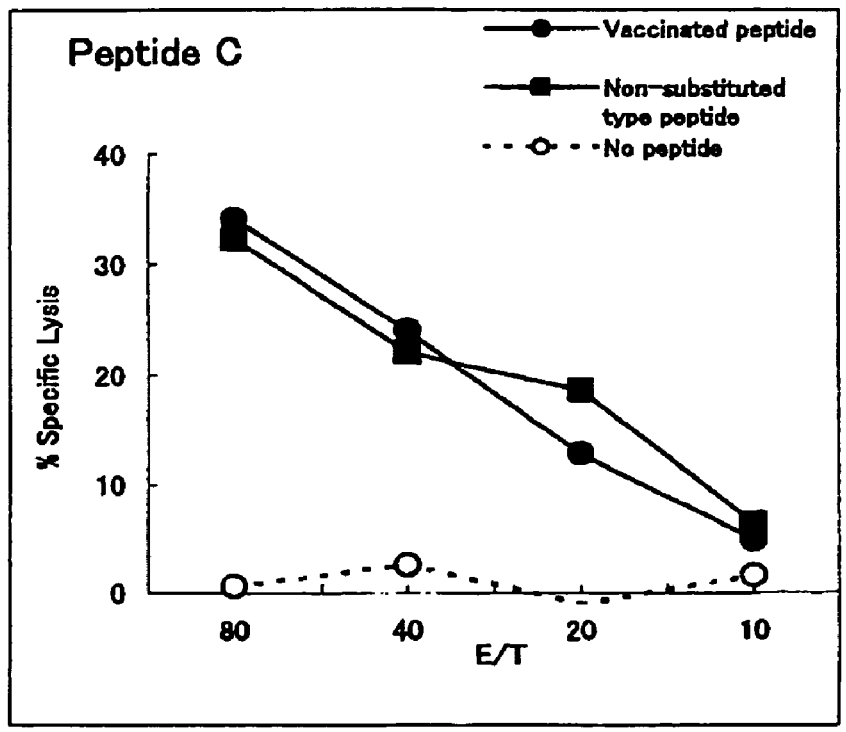
FIG. 8 is a graph showing the results of the test for cross-reactivity of the effector cells induced by the substituted type peptide, peptide C to the non-substituted type peptide, peptide A. In the figure, the vertical axis shows CTL-inducing activity (% Specific Lysis), and the horizontal axis shows E/T ratio. Also, in the figure, the solid circle shows the results obtained using target cells pulsed with peptide C, the solid square shows the results obtained using target cells pulsed with peptide A, and the open circle shows the results obtained using cells not pulsed with any peptide.
Figure 9:
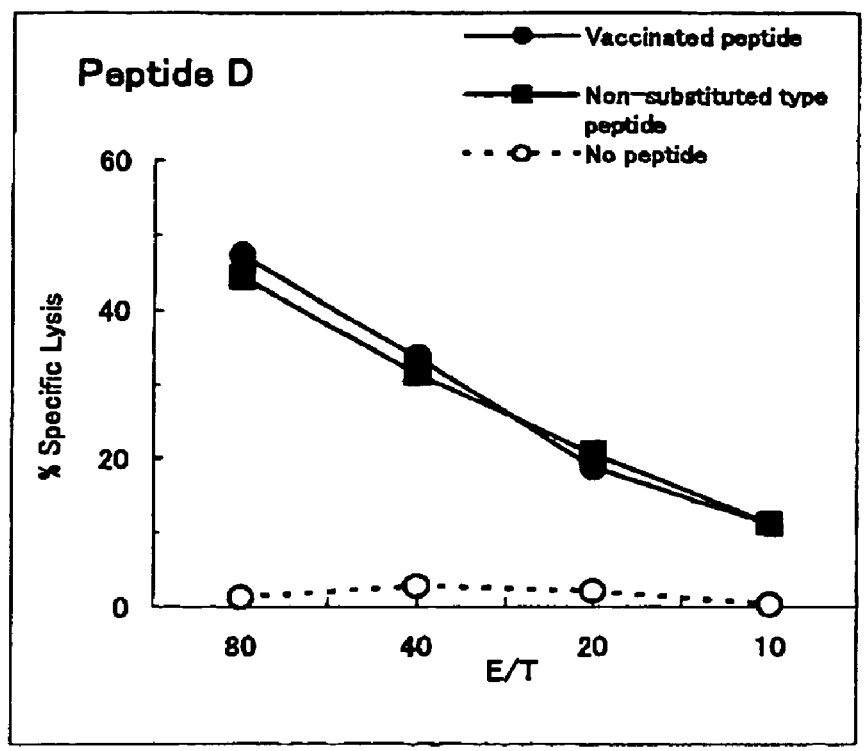
FIG. 9 is a graph showing the results of the test for cross-reactivity of the effector cells induced by the substituted type peptide, peptide D to the non-substituted type peptide, peptide A. In the figure, the vertical axis shows CTL-inducing activity (% Specific Lysis), and the horizontal axis shows E/T ratio. Also, in the figure, the solid circle shows the results obtained using target cells pulsed with peptide D, the solid square shows the results obtained using target cells pulsed with peptide A, and the open circle shows the results obtained using cells not pulsed with any peptide.
Figure 10:
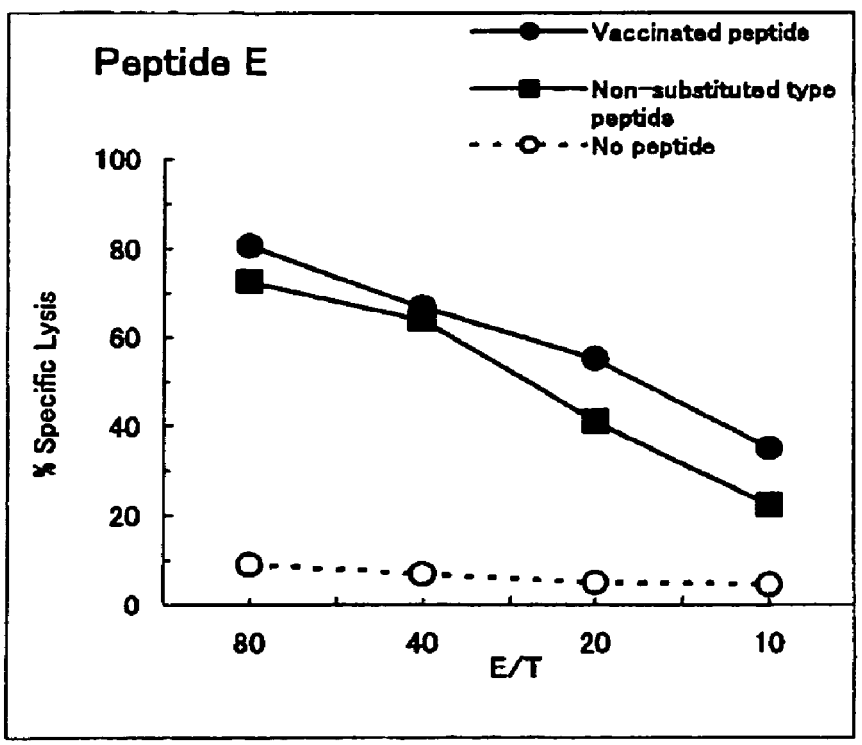
FIG. 10 is a graph showing the results of the test for cross-reactivity of the effector cells induced by the substituted type peptide, peptide E to the non-substituted type peptide, peptide A. In the figure, the vertical axis shows CTL-inducing activity (% Specific Lysis), and the horizontal axis shows E/T ratio. Also, in the figure, the solid circle shows the results obtained using target cells pulsed with peptide E, the solid square shows the results obtained using target cells pulsed with peptide A, and the open circle shows the results obtained using cells not pulsed with any peptide.
Figure 11:
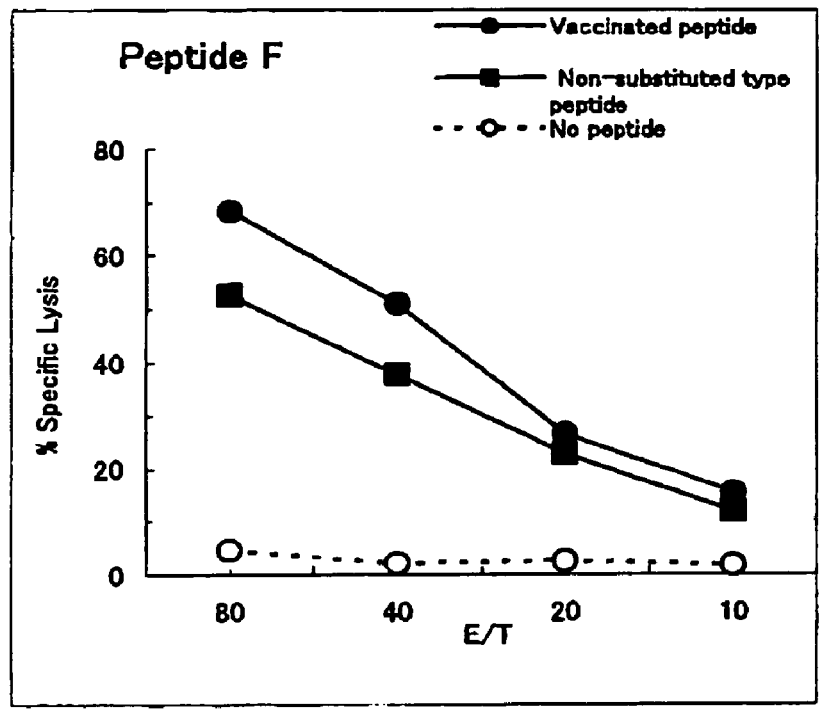
FIG. 11 is a graph showing the results of the test for cross-reactivity of the effector cells induced by the substituted type peptide, peptide F to the non-substituted type peptide, peptide A. In the figure, the vertical axis shows CTL-inducing activity (% Specific Lysis), and the horizontal axis shows E/T ratio. Also, in the figure, the solid circle shows the results obtained using target cells pulsed with peptide F, the solid square shows the results obtained using target cells pulsed with peptide A, and the open circle shows the results obtained using cells not pulsed with any peptide.
Figure 12:
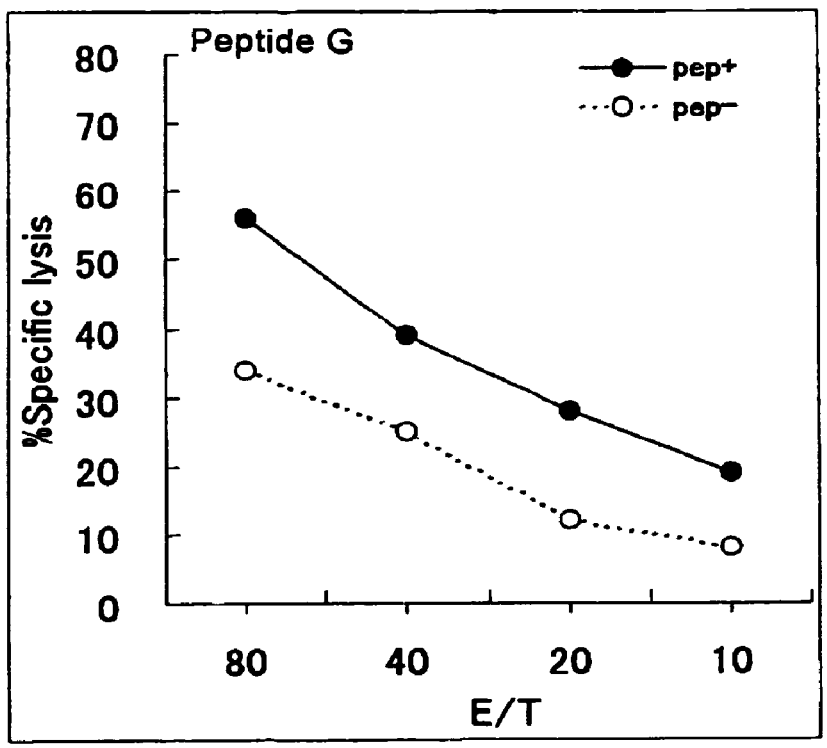
FIG. 12 is a graph showing that specific CTLs were induced when an HLA-A24-expressing transgenic mouse was immunized with peptide G wherein the cysteine residue at position 1 in WT1$_{235-243}$ is substituted with a serine residue. In the figure, the vertical axis shows cytotoxic activity (% Specific Lysis), and the horizontal axis shows E/T ratio. In the figure, the solid circle shows the results obtained using target cells pulsed with peptide G, and the open circle shows the results obtained using cells not pulsed with any peptide.
Figure 13:
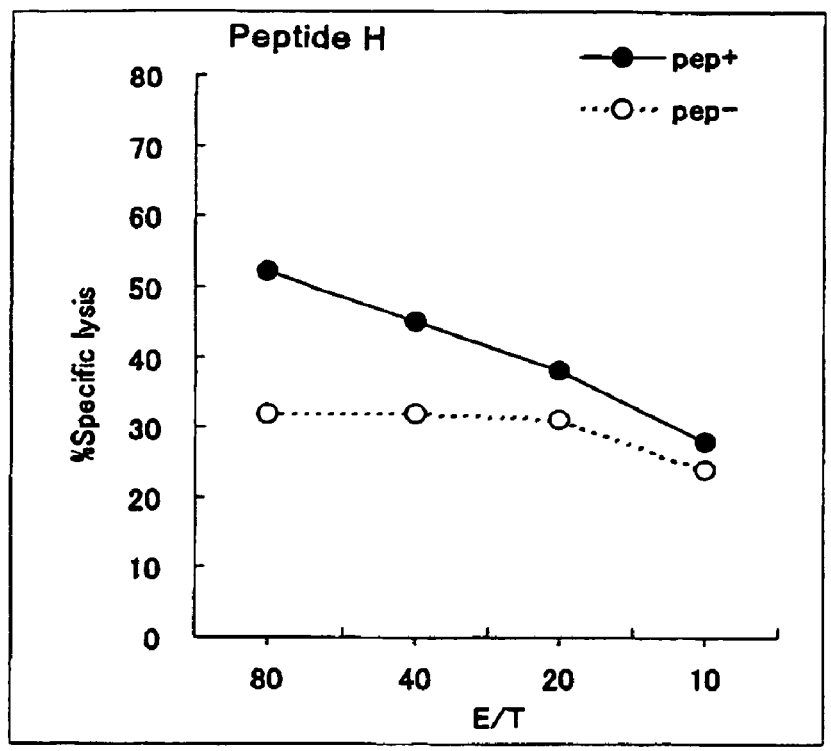
FIG. 13 is a graph showing that specific CTLs were induced when an HLA-A24-expressing transgenic mouse was immunized with peptide H wherein the cysteine residue at position 1 in WT1$_{235-243}$ is substituted with an alanine residue. In the figure, the vertical axis shows cytotoxic activity (% Specific Lysis), and the horizontal axis shows E/T ratio. In the figure, the solid circle shows the results obtained using target cells pulsed with peptide H, and the open circle shows the results obtained using cells not pulsed with any peptide.
Figure 14:
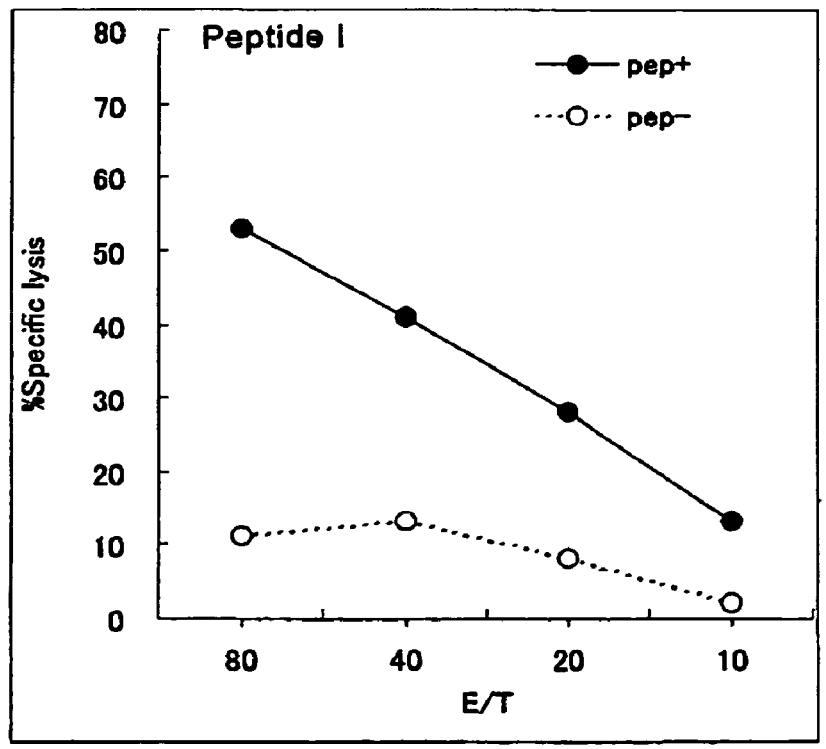
FIG. 14 is a graph showing that specific CTLs were induced when an HLA-A24-expressing transgenic mouse was immunized with peptide I wherein the cysteine residue at position 1 in peptide A is substituted with an ornithine residue. In the figure, the vertical axis shows cytotoxic activity (% Specific Lysis), and the horizontal axis shows E/T ratio. In the figure, the solid circle shows the results obtained using target cells pulsed with peptide I, and the open circle shows the results obtained using cells not pulsed with any peptide.
Figure 15:
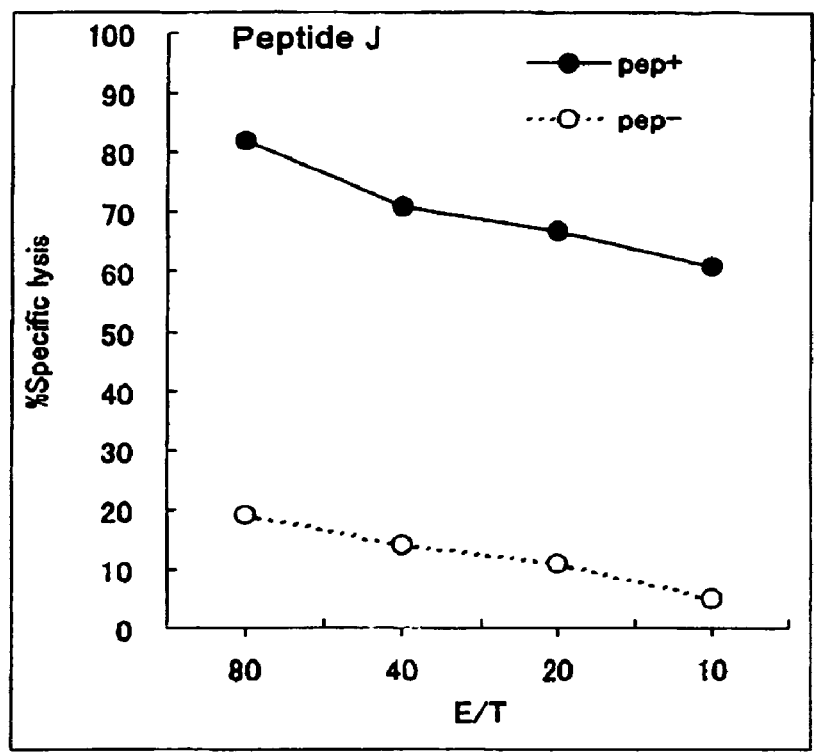
FIG. 15 is a graph showing that specific CTLs were induced when an HLA-A24-expressing transgenic mouse was immunized with peptide J wherein the cysteine residue at position 1 in peptide A is substituted with a citrulline residue. In the figure, the vertical axis shows cytotoxic activity (% Specific Lysis), and the horizontal axis shows E/T ratio. In the figure, the solid circle shows the results obtained using target cells pulsed with peptide J, and the open circle shows the results obtained using cells not pulsed with any peptide.

As used in the specification and the drawings of the present application, the following abbreviations are used for each amino acid residue.
Ala: alanine residue
Arg: arginine residue
Asn: asparagine residue
Asp: asparatic acid residue
Cys: cysteine residue
Gln: glutamine residue
Glu: glutamic acid residue
Gly: glycine residue
His: histidine residue
Ile: isoleucine residue
Leu: leucine residue
Lys: lysine residue
Met: methionine residue
Phe: phenylalanine residue
Pro: proline residue
Ser: serine residue
Thr: threonine residue
Trp: tryptophan residue
Tyr: tyrosine residue
Val: valine residue
Abu: 2-aminobutyric acid residue (also may be referred to as α-aminobutyric acid residue)
Orn: ornithine residue
Cit: citrulline residue An optical isomer may exist for the amino acid residues as shown above, and such an amino acid may be L- and D-isomer with L-isomer being preferred.

As used herein, the amino acid sequence of a peptide is depicted according to the conventional manner, in which the amino acid residue at the N-terminus is described on the left, whereas the amino acid residue at the C-terminus is described on the right.

(I) Peptides According to the Present Invention

Peptides of the present invention are derived from human WT1 (*Cell.*, 60:509, 1990, NCBI database Accession No. XP_034418, SEQ ID NO: 1), and have an activity to induce CTLs (an immunogenicity) in an HLA-A24-restriced manner.

The peptides of the invention may possibly undergo the processing in an antigen-presenting cell to generate cancer antigen peptides, which are then bound to an HLA-A24 antigen, and presented on the antigen-presenting cell, thereby inducing CTLs. Such a property may be examined using animal models for an HLA-A24 described in WO02/47474, and *Int J. Cancer:* 100,565-570 (2002).

The peptide of the invention comprises an amino acid sequence of the formula:

```
X-Y-Thr-Trp-Asn-Gln-Met-Asn-Leu      (SEQ ID NO: 4)
``` wherein X represents Ser, Ala, Abu, Arg, Lys, Orn, Cit, Leu, Phe, or Asn, and Y represents Tyr or Met, and has an activity to induce CTLs. Specifically, the peptide of the invention comprises any one of the amino acid sequences selected from a group consisting of:

```
                                     (SEQ ID NO: 5)
Ser Tyr Thr Trp Asn Gln Met Asn Leu, (SEQ ID NO: 6)
Ala Tyr Thr Trp Asn Gln Met Asn Leu, (SEQ ID NO: 7)
Abu Tyr Thr Trp Asn Gln Met Asn Leu, (SEQ ID NO: 8)
Arg Tyr Thr Trp Asn Gln Met Asn Leu, (SEQ ID NO: 9)
Lys Tyr Thr Trp Asn Gln Met Asn Leu, (SEQ ID NO: 10)
Orn Tyr Thr Trp Asn Gln Met Asn Leu, (SEQ ID NO: 11)
Cit Tyr Thr Trp Asn Gln Met Asn Leu, (SEQ ID NO: 12)
Leu Tyr Thr Trp Asn Gln Met Asn Leu, (SEQ ID NO: 13)
Phe Tyr Thr Trp Asn Gln Met Asn Leu, (SEQ ID NO: 14)
Asn Tyr Thr Trp Asn Gln Met Asn Leu, (SEQ ID NO: 15)
Ser Met Thr Trp Asn Gln Met Asn Leu, (SEQ ID NO: 16)
Ala Met Thr Trp Asn Gln Met Asn Leu, (SEQ ID NO: 17)
Abu Met Thr Trp Asn Gln Met Asn Leu, (SEQ ID NO: 18)
Arg Met Thr Trp Asn Gln Met Asn Leu, (SEQ ID NO: 19)
Lys Met Thr Trp Asn Gln Met Asn Leu, (SEQ ID NO: 20)
Orn Met Thr Trp Asn Gln Met Asn Leu, (SEQ ID NO: 21)
Cit Met Thr Trp Asn Gln Met Asn Leu, (SEQ ID NO: 22)
Leu Met Thr Trp Asn Gln Met Asn Leu, (SEQ ID NO: 23)
Phe Met Thr Trp Asn Gln Met Asn Leu,
and (SEQ ID NO: 24)
Asn Met Thr Trp Asn Gln Met Asn Leu,
``` and has an activity to induce CTLs. Among them, a peptide that comprises any one of the amino acid sequences selected from a group consisting of: SEQ ID NO: 5, 6, 7, 8, 9, 10, 11, 12, 13, 14, 15, and 16 is preferred.

The peptides of the invention that comprise an amino acid sequence of SEQ ID NO: 4 are not limited in any respect as long as the peptides have a property that a cancer antigen peptide derived from the peptide is presented on an antigen-presenting cell to induce CTLs. Typical length of the amino acid residues of the peptide is usually 9 to 100, preferably 9 to 50, more preferably 9 to 30, still more preferably 9 to 20, and even more preferably 9 to 11. In this context, a cancer antigen peptide is defined as a peptide that causes a CTL-inducing activity when bound to an HLA antigen, and presented on an antigen-presenting cell.

The peptides of the invention may be prepared according to a method usually used in peptide chemistry. Examples of such preparations are those as described in the literatures including "Peptide Synthesis", Interscience, New York, 1966; "The Proteins", Vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

The peptides of the invention may be also prepared on the basis of the sequence information of polynucleotide encoding the peptide of the invention according to conventional DNA synthesis and genetic engineering procedures. Procedures such as the DNA synthesis, constructions of various plasmids, transfection of the same into host cells, cultivation of the transformants, and recovery of the proteins from the culture may be carried out according to methods well-known by those skilled in the art, methods described in the literatures (Molecular Cloning, T.Maniatis et al., CSH Laboratory (1983), DNA Cloning, D M. Glover, IRL PRESS(1985)), or the method described (II) hereinafter.

Specific illustrations of the peptides according to the invention are provided below.

As described above, the present invention is based on the new finding that substituted type peptides wherein the cysteine residue at position 1 in a natural type peptide derived from WT1, $WT1_{235-243}$ (SEQ ID NO: 2), or a peptide altered in the position 2 of the peptide, $WT1_{235-243}$ (2M→Y) (SEQ ID NO: 3) is substituted with serine residue, alanine residue, arginine residue, lysine residue, leucine residue, phenylalanine residue, asparagine residue, 2-aminobutyric acid residue (α-aminobutyric acid residue), ornithine residue, or citrulline residue, have an activity to induce CTLs in vivo. Peptides according to the invention that comprise any one of those substituted type peptides are useful as an active ingredient comprised in a composition for inducing CTLs or a cancer vaccine as used in immunotherapy for cancer.

Examples of more specific peptides according to the invention include the peptides as shown in (1-1) to (1-4) below.

(1-1) Cancer Antigen Peptides which Consist of an Amino Acid Sequence of SEQ ID NO: 4

Specific examples of the peptides according to the invention include cancer antigen peptides which consist of an amino acid sequence of SEQ ID NO: 4. The cancer antigen peptides which consist of an amino acid sequence of SEQ ID NO: 4 specifically include a cancer antigen peptide that consists of an amino acid sequence selected from the group consisting of

```
                                     (SEQ ID NO: 5)
Ser Tyr Thr Trp Asn Gln Met Asn Leu, (SEQ ID NO: 6)
Ala Tyr Thr Trp Asn Gln Met Asn Leu,
```

-continued

```
                                                 (SEQ ID NO: 7)
Abu Tyr Thr Trp Asn Gln Met Asn Leu, (SEQ ID NO: 8)
Arg Tyr Thr Trp Asn Gln Met Asn Leu, (SEQ ID NO: 9)
Lys Tyr Thr Trp Asn Gln Met Asn Leu, (SEQ ID NO: 10)
Orn Tyr Thr Trp Asn Gln Met Asn Leu, (SEQ ID NO: 11)
Cit Tyr Thr Trp Asn Gln Met Asn Leu, (SEQ ID NO: 12)
Leu Tyr Thr Trp Asn Gln Met Asn Leu, (SEQ ID NO: 13)
Phe Tyr Thr Trp Asn Gln Met Asn Leu, (SEQ ID NO: 14)
Asn Tyr Thr Trp Asn Gln Met Asn Leu, (SEQ ID NO: 15)
Ser Met Thr Trp Asn Gln Met Asn Leu, (SEQ ID NO: 16)
Ala Met Thr Trp Asn Gln Met Asn Leu, (SEQ ID NO: 17)
Abu Met Thr Trp Asn Gln Met Asn Leu, (SEQ ID NO: 18)
Arg Met Thr Trp Asn Gln Met Asn Leu, (SEQ ID NO: 19)
Lys Met Thr Trp Asn Gln Met Asn Leu, (SEQ ID NO: 20)
Orn Met Thr Trp Asn Gln Met Asn Leu, (SEQ ID NO: 21)
Cit Met Thr Trp Asn Gln Met Asn Leu, (SEQ ID NO: 22)
Leu Met Thr Trp Asn Gln Met Asn Leu, (SEQ ID NO: 23)
Phe Met Thr Trp Asn Gln Met Asn Leu,
and
                                                 (SEQ ID NO: 24)
Asn Met Thr Trp Asn Gln Met Asn Leu.
```

Among them, a cancer antigen peptide consisting of the amino acid sequence of SEQ ID NO: 5, a cancer antigen peptide consisting of the amino acid sequence of SEQ ID NO: 6, a cancer antigen peptide consisting of the amino acid sequence of SEQ ID NO: 7, a cancer antigen peptide consisting of the amino acid sequence of SEQ ID NO: 8, a cancer antigen peptide consisting of the amino acid sequence of SEQ ID NO: 9, a cancer antigen peptide consisting of the amino acid sequence of SEQ ID NO: 10, a cancer antigen peptide consisting of the amino acid sequence of SEQ ID NO: 11, a cancer antigen peptide consisting of the amino acid sequence of SEQ ID NO: 12, a cancer antigen peptide consisting of the amino acid sequence of SEQ ID NO: 13, a cancer antigen peptide consisting of the amino acid sequence of SEQ ID NO: 14, a cancer antigen peptide consisting of the amino acid sequence of SEQ ID NO: 15, and a cancer antigen peptide consisting of the amino acid sequence of SEQ ID NO: 16, are preferred.

Those peptides may be prepared according to common methods for peptide synthesis as described above. The activity of those peptides to induce CTLs may be determined in animal models for human described in WO 02/47474, and *Int J. Cancer:* 100, 565-570 (2002).

(1-2) Cancer Antigen Peptides which Comprise an Amino Acid Sequence of SEQ ID NO: 4, and which Contain the Motif Structure It has been known that lots of subtypes exist in HLA molecules, and that the amino acid sequences of antigen peptides that bind to each subtype obey a certain rule (binding motif). It has been also known that, regarding the binding motif for HLA-A24, the amino acid residue at position 2 is tyrosine residue (Tyr), phenylalanine residue (Phe), methionine residue (Met), or tryptophan residue (Trp), and the amino acid at the C-terminus is phenylalanine residue (Phe), leucine residue (Leu), isoleucine residue (Ile), tryptophan residue (Trp), or methionine residue (Met) in the peptides consisting of 8 to 11 amino acid residues. (*J. Immunol.*, 152, p 3913, 1994, *Immunogenetics*, 41, p 178, 1995, *J. Immunol.*, 155, p 4307, 1994).

Based on the rule, examples of the peptides according to the invention also include cancer antigen peptides comprising an amino acid sequence of SEQ ID NO: 4, and containing the motif structure. Specifically, they include peptides consisting of 10 amino acid residues wherein Phe, Leu, Ile, Trp, or Met is added to the C-terminus of a peptide shown in SEQ ID NO: 4, or peptides consisting of 11 amino acid residues wherein Phe, Leu, Ile, Trp, or Met is further added to the C-terminus of any one of said peptides consisting of 10 amino acid residues, all of which have an activity to induce CTLs.

More specific examples include peptides consisting of 10 amino acid residues wherein Phe, Leu, Ile, Trp, or Met is added to the C-terminus of a peptide consisting of 9 amino acid residues shown in the following:

```
                                                 (SEQ ID NO: 5)
Ser Tyr Thr Trp Asn Gln Met Asn Leu, (SEQ ID NO: 6)
Ala Tyr Thr Trp Asn Gln Met Asn Leu, (SEQ ID NO: 7)
Abu Tyr Thr Trp Asn Gln Met Asn Leu, (SEQ ID NO: 8)
Arg Tyr Thr Trp Asn Gln Met Asn Leu, (SEQ ID NO: 9)
Lys Tyr Thr Trp Asn Gln Met Asn Leu, (SEQ ID NO: 10)
Orn Tyr Thr Trp Asn Gln Met Asn Leu, (SEQ ID NO: 11)
Cit Tyr Thr Trp Asn Gln Met Asn Leu, (SEQ ID NO: 12)
Leu Tyr Thr Trp Asn Gln Met Asn Leu, (SEQ ID NO: 13)
Phe Tyr Thr Trp Asn Gln Met Asn Leu, (SEQ ID NO: 14)
Asn Tyr Thr Trp Asn Gln Met Asn Leu, (SEQ ID NO: 15)
Ser Met Thr Trp Asn Gln Met Asn Leu, (SEQ ID NO: 16)
Ala Met Thr Trp Asn Gln Met Asn Leu,
```

-continued

Abu Met Thr Trp Asn Gln Met Asn Leu, (SEQ ID NO: 17)

Arg Met Thr Trp Asn Gln Met Asn Leu, (SEQ ID NO: 18)

Lys Met Thr Trp Asn Gln Met Asn Leu, (SEQ ID NO: 19)

Orn Met Thr Trp Asn Gln Met Asn Leu, (SEQ ID NO: 20)

Cit Met Thr Trp Asn Gln Met Asn Leu, (SEQ ID NO: 21)

Leu Met Thr Trp Asn Gln Met Asn Leu, (SEQ ID NO: 22)

Phe Met Thr Trp Asn Gln Met Asn Leu, (SEQ ID NO: 23)
or

Asn Met Thr Trp Asn Gln Met Asn Leu, (SEQ ID NO: 24)

or peptides consisting of 11 amino acid residues wherein Phe, Leu, Ile, Trp, or Met is further added to the C-terminus of any one of said peptides consisting of 10 amino acid residues, all of which have an activity to induce CTLs.

Preferred peptides include those consisting of 10 amino acid residues wherein Phe, Leu, Ile, Trp, or Met is added to the C-terminus of a peptide shown in SEQ ID NO: 5, 6, 7, 8, 9, 10, 11, 12, 13, 14, 15, or 16, or peptides consisting of 11 amino acid residues wherein Phe, Leu, Ile, Trp, or Met is further added to the C-terminus of any one of said peptides consisting of 10 amino acid residues, all of which have an activity to induce CTLs.

Those peptides as shown above may be also prepared according to common methods for peptide synthesis as described above. The activity of those peptides to induce CTLs may be determined in animal models for human described in WO 02/47474, and *Int J. Cancer:* 100, 565-570 (2002).

(1-3) Epitope Peptides which Comprise an Amino Acid Sequence of SEQ ID NO: 4

Recently, it has been demonstrated that a peptide wherein many CTL epitopes (antigen peptides) are linked each other (an epitope peptide) has an activity to induce effectively CTLs. For example, *Journal of Immunology* 1998, 161: 3186-3194 describes that the about 30-mer peptide wherein HLA-A2, -A3, -A11, B53-restricted CTL epitopes derived from a cancer antigen protein, PSA, are linked each other induced CTLs specific for the relevant CTL epitope in vivo.

Also, it has been demonstrated that a peptide (epitope peptide) wherein a CTL epitope and a helper epitope are linked each other effectively induced CTLs. Helper epitope refers to as a peptide that has an activity to activate CD4-positive T cells (*Immunity.*, 1:751, 1994), and is known to include HBVc128-140 derived from hepatitis B virus and TT947-967 derived from tetanus toxin. CD4-positive T cells activated by the helper epitope are believed to be important in immune responses to destroy tumors because they exert the actions such as the induction of CTL differentiation and the maintenance of CTLs, and the activation of effectors including a macrophage. As examples of such peptides wherein a helper epitope and a CTL epitope are linked each other, *Journal of Immunology* 1999, 162: 3915-3925, for example, describes that a DNA encoding the peptide linked with the six HLA-A2-restricted antigen peptides, the three HLA-A11-restricted antigen peptides derived from HBV, and a helper epitope (minigene) effectively induced CTLs in response to the relevant epitopes in vivo. In addition, the peptide wherein the CTL epitope (cancer antigen peptide consisting of positions 280 to 288 of a melanoma antigen, gp100) and the helper epitope (T helper epitope derived from tetanus toxin) are linked each other has been tested in clinical trial (*Clinical Cancer Res.,* 2001, 7: 3012-3024).

Based on these facts, a peptide (epitope peptide) wherein various epitopes including the cancer antigen peptides of the present invention as shown in (1-1) or (1-2) above are linked, which has an activity to induce CTLs in vivo, is also exemplified as the peptides according to the invention.

In this context, an epitope peptide refers to as a peptide of either one wherein many CTL epitopes (antigen peptides) are linked each other (1), or one wherein a CTL epitope and a helper epitope are linked each other (2), both of which undergo the processing in an antigen-presenting cell to generate cancer antigen peptides, which are then presented on the antigen-presenting cell, thereby inducing CTLs.

In case that an epitope to be linked with the cancer antigen peptide of the invention is a CTL epitope, usable CLT epitopes include those derived from WT1 which are restricted for HLA-A1, -A0201, -A0204, -A0205, -A0206, -A0207, -A11, -A24, -A31, -A6801, -B7, -B8, -B2705, -B37, -Cw0401, -Cw0602, or the like. Two or more CTL epitopes may be linked each other, and one CTL epitope may be 8 to 14 amino acid residues in length on the basis of the analysis of antigen peptides bound to various HLA molecules (*Immunogenetics,* 41:178, 1995).

In case that an epitope to be linked with the cancer antigen peptide of the invention is a helper epitope, HBVc128-140 derived from hepatitis B virus and TT947-967 derived from tetanus toxin as described above may be exemplified. The length of the helper epitope may be about 13 to about 30, preferably about 13 to about 17 amino acid residues.

Specific examples of the epitope peptides according to the invention include epitope peptides wherein one or more peptides consisting of an amino acid sequence of any one of SEQ ID NOs: 5, 6, 7, 8, 9, 10, 11, 12, 13, 14, 15, 16, 17, 18, 19, 20, 21, 22, 23, and 24 are linked with a helper epitope. More specifically, an epitope peptide wherein one or more peptides consisting of an amino acid sequence of any one of SEQ ID NOs: 5, 6, 7, 8, 9, 10, 11, 12, 13, 14, 15, and 16 are linked with a helper epitope derived from tetanus toxin (for example, Phe Asn Asn Phe Thr Val Ser Phe Trp Leu Arg Val Pro Lys Val Ser Ala Ser His Leu Glu; SEQ ID NO: 25), and an epitope peptide wherein one or more peptide of an amino acid sequence of any one of SEQ ID NOs: 5, 6, 7, 8, 9, 10, 11, 12, 13, 14, 15, and 16 are linked with Ala Gln Tyr Ile Lys Ala Asn Ser Lys Phe Ile Gly Ile Thr Glu Leu (SEQ ID NO: 26, *Clinical Cancer Res.,* 2001, 7: 3012-3024) are exemplified.

Those epitope peptides wherein various epitopes are linked each other may be prepared according to common methods for peptide synthesis as described above. The peptides may be also prepared on the basis of the sequence information of polynucleotide encoding the peptide wherein various epitopes are linked each other according to conventional DNA synthesis and genetic engineering procedures. Namely, the epitope peptides may be prepared by inserting the polynucleotide into a well-known expression vector, transforming a host cell with the resultant recombinant expression vector, culturing the transformants, and recovering the epitope peptide wherein various intended epitopes are linked each other from the culture. Those procedures may be carried out according to methods described in the literatures (Molecular Cloning, T. Maniatis et al., CSH Laboratory(1983), DNA Cloning, D M. Glover, IRL PRESS (1985)), or the method described in (II) hereinafter.

The activity of the prepared epitope peptides wherein various epitopes are linked each other may be determined for the CTL-inducing activity by means of an assay using animal models for human described in WO 02/47474, and *Int J. Cancer:* 100, 565-570 (2002).

(1-4) Peptides which Comprise an Amino Acid Sequence of SEQ ID NO: 4 wherein the Amino Group of the N-terminal Amino Acid or the Carboxyl Group of the C-terminal Amino Acid is Modified Further, it is possible to modify the amino group of the N-terminal amino acid or the carboxyl group of the C-terminal amino acid in the peptides of the invention as described in (1-1) to (1-3) above.

In this context, modifying groups of the amino group of the N-terminal amino acid include an alkyl group having 1 to 6 carbon atoms, a phenyl group, a cycloalkyl group, an acyl group, and the like, of which the 1 to 3 groups may be selected. Examples of the acyl group include an alkanoyl group having 1 to 6 carbon atoms, an alkanoyl group having 1 to 6 carbon atoms substituted with a phenyl group, a carbonyl group substituted with a cycloalkyl group having 5 to 7 carbon atoms, an alkylsulfonyl group having 1 to 6 carbon atoms, a phenylsulfonyl group, an alkoxycarbonyl group having 2 to 6 carbon atoms, an alkoxycarbonyl group substituted with a phenyl group, a carbonyl group substituted with a cycloalkoxy having 5 to 7 carbon atoms, a phenoxycarbonyl group, and the like.

Peptides wherein the carboxyl group of the C-terminal amino acid is modified include esters and amides. Specific esters include a C1-C6 alkyl ester, a C0-C6 alkyl ester substituted with a phenyl group, a C5-C7 cycloalkyl ester, and the like, whereas specific amides include an amide, an amide substituted with one or two C1-C6 alkyl groups, an amide substituted with one or two C0-C6 alkyl groups substituted with a phenyl group, an amide that forms a 5 to 7-numbered azacycloalkane that contains the nitrogen atom of the amide, and the like.

The peptides of the invention are useful, for example, 1) as an active ingredient comprised in a composition for inducing CTLs or a cancer vaccine described hereinafter, or 2) in the preparation of antigen-presenting cells described hereinafter.

(II) Polynucleotides, Expression Vectors, and Transformants of the Present Invention The invention also provides polynucleotides encoding the peptides of the invention described above. The polynucleotides encoding the peptides of the invention may be in a form of either DNA or RNA. Those polynucleotides may be readily prepared on the basis of the information on amino acid sequences of the peptides of the invention, and on DNAs encoding the same. Specifically, they may be prepared according to common methods for DNA synthesis, or PCR amplification.

Examples of the polynucleotides of the invention include a polynucleotide that encodes a peptide comprising an amino acid sequence of SEQ ID NO: 4, and having an activity to induce CTLs. Specific examples of the polynucleotides include a polynucleotide that encodes a peptide comprising any one of the amino acid sequences selected from the group consisting of SEQ ID NOs: 5, 6, 7, 8, 9, 10, 11, 12, 13, 14, 15, 16, 17, 18, 19, 20, 21, 22, 23, and 24, and having an activity to induce CTLs. Among them, a polynucleotide that encodes a peptide comprising any one of the amino acid sequences selected from the group consisting of SEQ ID NOs: 5, 6, 7, 8, 9, 10, 11, 12, 13, 14, 15, and 16, and having an activity to induce CTLs is preferred.

Specifically, a polynucleotide that encodes an epitope peptide comprising an amino acid sequence of SEQ ID NO: 4 as described in (1-3) above is exemplified. More specifically, a polynucleotide that encodes an epitope peptide comprising an amino acid sequence of any one of SEQ ID NOs: 5, 6, 7, 8, 9, 10, 11, 12, 13, 14, 15, 16, 17, 18, 19, 20, 21, 22, 23, and 24 is exemplified. Still more specifically, polynucleotides that encode an epitope peptide wherein one or more peptides consisting of an amino acid sequences of any one of SEQ ID NOs: 5, 6, 7, 8, 9, 10, 11, 12, 13, 14, 15, and 16 are linked with a helper epitope are exemplified, including a polynucleotide that encodes a peptide wherein one or more peptide consisting of an amino acid sequence of any one of SEQ ID NOs: 5, 6, 7, 8, 9, 10, 11, 12, 13, 14, 15, and 16 are linked with a helper epitope derived from tetanus toxin (for example, Phe Asn Asn Phe Thr Val Ser Phe Trp Leu Arg Val Pro Lys Val Ser Ala Ser His Leu Glu; SEQ ID NO: 25), and a peptide wherein one or more peptide consisting of an amino acid sequence of any one of SEQ ID NOs: 5, 6, 7, 8, 9, 10, 11, 12, 13, 14, 15, and 16 are linked with Gln Tyr Ile Lys Ala Asn Ser Lys Phe Ile Gly Ile Thr Glu Leu (SEQ ID NO: 26, *Clinical Cancer Res.,* 2001, 7: 3012-3024).

The polynucleotides of the present invention thus prepared may be inserted into an expression vector to prepare recombinant expression vectors for expression of the peptides of the invention.

Expression vectors as used herein may be selected as appropriate depending on the host and the purpose in usage, and include a plasmid, a phage vector, and a virus vector.

Examples of vectors as used for *Escherichia coli* hosts include plasmid vectors such as pUC118, pUC119, pBR322, and pCR3, and phage vectors such as λZAPII, and λgt11. Examples of vectors as used for yeast hosts include pYES2, and pYEUra3. Examples of vectors as used for insect cell hosts include pAcSGHisNT-A. Examples of vectors as used for animal cell hosts include plasmid vectors such as pKCR, pCDM8, pGL2, pcDNA3.1, pRc/RSV, and pRc/CMV, and virus vectors such as a retrovirus vector, an adenovirus vector, and an adeno-associated virus vector.

Those vectors may comprise a factor such as a promoter capable of inducing the expression, a gene encoding a signal sequence, a selection marker gene, a terminator, or the like, if necessary.

Also, the vectors may comprise an additional sequence for expressing a protein as a fusion protein with thioredoxin, His-tag, or GST (glutathione S-transferase) for easy isolation and purification. In this case, a vector for expression of a GST-fusion protein that comprises a promoter (lac, tac, trc, trp, CMV, SV40 early promoter, or the like) suitably operated in a host cell (i.e., pGEX4T), a vector that comprises a tag-sequence such as Myc, His (i.e., pcDNA3.1/Myc-His), and a vector that expresses a fusion protein comprising thioredoxin or His-tag (pET32a) may be used.

The CTL-inducing activity of the polynucleotides of the present invention or the expression vectors comprising the same may be determined in animal models for human described in WO 02/47474, and *Int J. Cancer.* 100, 565-570 (2002).

The polynucleotides or the expression vectors comprising the same of the invention are useful, for example, 1) in the preparation of the peptides of the invention as described hereinafter, 2) in gene therapy as described hereinafter, or 3) in the preparation of antigen-presenting cells as described hereinafter.

The expression vectors thus prepared of the invention may be transformed into hosts to prepare transformants that comprise the expression vectors.

Hosts as used herein include *Escherichia coli*, a yeast, an insect cell, and an animal cell. *Escherichia coli* includes *E. coli* K-12 lines such as HB101 strain, C600 strain, JM109 strain, DH5α strain, and AD494(DE3) strain. Yeasts include *Saccharomyces cerevisiae*. Animal cells include L929 cell, BALB/c3T3 cell, C127 cell, CHO cell, COS cell, Vero cell, and Hela cell. Insect cells include sf9.

Common methods for transformation suitable for respective host cells may be used to transform the host cells with an expression vector. Specific methods include calcium phosphate method, DEAE-dextran method, electroporation, and a method wherein a lipid for gene transfer is used (Lipofectamine, Lipofectin; Gibco-BRL). After the transformation, the transformants may be incubated in a conventional medium containing a selection marker to select transformants wherein the expression vector as described above has been transformed into a host cell.

The transformants thus prepared may be incubated in an appropriate condition to prepare the peptides of the invention. The polypeptide may be further isolated and purified according to common procedures for biochemical purifications. Examples of procedures for the purification include salt precipitation, ion-exchange chromatography, adsorption chromatography, affinity chromatography, and gel filtration chromatography. When a polypeptide of the invention is expressed as a fusion protein comprising thioredoxin, His-tag, GST, or the like, the polypeptide may be isolated and purified by a purification method based on a property of such fusion protein or tag.

(III) Antibodies of the Present Invention

The present invention provides antibodies which specifically bind to a peptide according to the invention. The antibodies of the invention are not limited to a specific antibody, and may be a polyclonal antibody or a monoclonal antibody directed to a peptide of the invention as an immune antigen.

As mentioned above, the antibodies of the invention are not limited to a specific antibody as long as they specifically bind to the peptide of the invention, and specific examples include an antibody that specifically binds to a peptide consisting of any one of the amino acid sequences selected from SEQ ID NOs: 5, 6, 7, 8, 9, 10, 11, 12, 13, 14, 15, 16, 17, 18, 19, 20, 21, 22, 23, and 24, and having an activity to induce CTLs. Among them, antibodies that specifically bind to a peptide consisting of any one of the amino acid sequences selected from SEQ ID NOs: 5, 6, 7, 8, 9, 10, 11, 12, 13, 14, 15, and 16 are preferred.

Preparations for antibodies have been well known, and the antibodies of the invention may be prepared according to common methods well-known in the art (Current protocols in Molecular Biology edit. Ausubel et al. (1987) Publish. John Wiley and Sons. Section 11.12 to 11.13, Antibodies; A Laboratory Manual, Lane, H, D. et al. ed., Cold Spring Harbor Laboratory Press Publisher, New York 1989).

Specifically, the antibodies may be prepared using the peptides of the invention (for example, a cancer antigen peptide consisting of any one of the amino acid sequences selected from SEQ ID NOs: 5, 6, 7, 8, 9, 10, 11, 12, 13, 14, 15, and 16) as an immunogen to immunize a non-human animal such as a rabbit, followed by obtaining the antibodies from the serum of the immunized animal in a conventional manner. On the other hand, monoclonal antibodies may be prepared by immunizing a non-human animal such as a mouse with a peptide of the invention (for example, a cancer antigen peptide consisting of any one of the amino acid sequences selected from SEQ ID NOs: 5, 6, 7, 8, 9, 10, 11, 12, 13, 14, 15, and 16), and preparing hybridoma from the splenocytes obtained and myeloma cells by cell fusion, followed by obtaining the antibodies from the hybridoma (Current protocols in Molecular Biology edit. Ausubel et al. (1987) Publish. John Wiley and Sons. Section 11.4 to 11.11).

The antibodies directed to the peptides of the invention may be prepared in a manner that the immunological reaction is enhanced using diverse adjuvants suitable for the host. Examples of the adjuvants include Freund's adjuvant, mineral gels such as aluminium hydroxide, surfactants such as lysolecithin, Pluronic polyol, polyanions, peptides, oil emulsions, Keyhole limpet Hemocyanin, and dinitrophenol, and human adjuvants such as BCG (*Bacille Calmette Guerin*) and *Corynebacterium-parvum*.

As described above, the antibodies that recognize the peptide, as well as the antibodies that neutralize the activity of the peptide may be readily prepared by immunizing appropriately an animal with the peptides of the invention in a conventional manner. Such antibodies may be used in affinity chromatography, immunological diagnosis, and the like. Immunological diagnosis may be selected as appropriate from immunoblotting, radioimmunoassay (RIA), enzyme-linked immunosorbent assay (ELISA), a fluorescent or luminescent assay, and the like. The immunological diagnosis is useful to diagnose cancers wherein the WT1 gene is expressed, such as gastric cancer, colon cancer, lung cancer, breast cancer, embryonal cancer, skin cancer, bladder cancer, prostate cancer, uterine cancer, cervical cancer, and ovarian cancer.

(IV) Antigen-presenting Cells of the Present Invention

The invention provides antigen-presenting cells on which a complex between a cancer antigen peptide derived from the peptide according to the invention and an HLA-A24 antigen is presented.

Examples described hereinafter demonstrate that the administration of the peptides of the invention induces CTLs, showing that antigen-presenting cells on which a complex between a cancer antigen peptide derived from the peptide according to the invention and an HLA-A24 antigen is presented, exist in peripheral blood mononuclear cells, and then CTLs are induced, which specifically recognize the cells presenting such a complex. Those antigen-presenting cells on which a complex between an HLA-A24 antigen and a cancer antigen peptide derived from the peptide according to the invention is presented, are useful in cell therapy (DC therapy) as described hereinafter.

Antigen-presenting cells according to the present invention are not limited to a specific cell as long as they presents on their surfaces a complex between a cancer antigen peptide derived from the peptide according to the invention and an HLA-A24 antigen. They specifically include antigen-presenting cells of dendritic cells on which a complex between a peptide consisting of an amino acid sequence of any one of SEQ ID NOs: 5, 6, 7, 8, 9, 10, 11, 12, 13, 14, 15, 16, 17, 18, 19, 20, 21, 22, 23, and 24 and having an activity to induce CTLs, and an HLA-A24 antigen is presented. Preferably, they include antigen-presenting cells of dendritic cells on which a complex between a cancer antigen peptide consisting of an amino acid sequence of any one of SEQ ID NOs: 5, 6, 7, 8, 9, 10, 11, 12, 13, 14, 15, and 16 and an HLA-A24 antigen is presented.

In order to prepare antigen-presenting cells as used in cell therapy (DC therapy), cells having an antigen-presenting ability are isolated from a cancer patient, and pulsed ex vivo with a peptide of the invention, or transformed with a polynucleotide of the invention or an expression vector comprising the same to present a complex between an HLA-A24 antigen and the cancer antigen peptide derived from the peptide of the invention. In this context, the "cell having an antigen-presenting ability" is not limited to a specific cell as long as it is a cell expressing on its cell surface an HLA-A24 antigen that allows a peptide of the invention to be presented, and dendritic cells, which is believed to have especially a high antigen-presenting ability, are preferably exemplified.

Substances to be pulsed to the cells having an antigen-presenting ability may be peptides of the invention, as well as polypeptides encoding the peptides of the present invention, and expression vectors comprising the same.

Antigen-presenting cells of the present invention may be prepared, for example, by isolating cells having an antigen-presenting ability from a cancer patient, pulsing the cells ex vivo with a peptide of the invention (e.g. the cancer antigen peptide consisting of an amino acid sequence of any one of SEQ ID NOs: 5, 6, 7, 8, 9, 10, 11, 12, 13, 14, 15, and 16), and preparing a complex between an HLA-A24 antigen and the cancer antigen peptide derived from the peptide of the invention (*Cancer Immunol. Immunother.,*46: 82,1998, *J. Immunol.,* 158: p 1796, 1997, *Cancer Res.,*59: p 1184, 1999). When dendritic cells are used, antigen-presenting cells of the present invention may be prepared, for example, by isolating lymphocytes from peripheral bloods of a cancer patient using Ficoll method, removing non-adherent cells, incubating the adherent cells in the presence of GM-CSF and IL-4 to induce dendritic cells, and incubating and pulsing the resultant dendritic cells with a peptide of the invention, or the like.

When antigen-presenting cells of the invention are prepared by transforming the cells having an antigen-presenting ability described above with a polynucleotide encoding the peptide of the invention (e.g., a polynucleotide encoding the peptide comprising an amino acid sequence of any one of SEQ ID NOs: 5, 6, 7, 8, 9, 10, 11, 12, 13, 14, 15, and 16), or with an expression vector comprising the same, such preparation of the polynucleotide in a form of DNA, may be conducted consulting, for example, *Cancer Res.,*56:p 5672, 1996, or *J. Immunol.,* 161: p 5607, 1998. Similarly, such preparation of the polynucleotide in a form of RNA also allows to prepare antigen-presenting cells, and then for example *J Exp. Med.,* 184:p 465, 1996 may be consulted.

The antigen-presenting cells thus prepared as described above are useful as an active ingredient comprised in a composition for inducing CTLs or a cancer vaccine, or in cell therapy (DC therapy) as described hereinafter.

(V) CTLs of the Present Invention

The present invention provides CTLs which recognize a complex between a cancer antigen peptide derived from the peptide of the invention and an HLA-A24 antigen.

Examples described hereinafter demonstrate that the administration of the peptides of the invention induces CTLs, showing that the antigen-presenting cells on which a complex between a cancer antigen peptide derived from the peptide of the invention and an HLA-A24 antigen is presented, exist in peripheral blood mononuclear cells, and then CTLs are induced, which specifically recognize cells on which such a complex is presented. Those CTLs that specifically recognize a complex between an HLA-A24 antigen and a cancer antigen peptide derived from the peptide of the invention are useful in adoptive immunotherapy as described hereinafter.

CTLs of the present invention are not limited to a specific CTL as long as they specifically recognize a complex between a cancer antigen peptide derived from the peptide of the invention and an HLA-A24 antigen, and particularly include CTLs specifically recognize a complex between a peptide consisting of an amino acid sequence of any one of SEQ ID NOs: 5, 6, 7, 8, 9, 10, 11, 12, 13, 14, 15, 16, 17, 18, 19, 20, 21, 22, 23, and 24 and having an activity to induce CTLs, and an HLA-A24 antigen. Among them, CTLs that specifically recognize a complex between a cancer antigen peptide consisting of an amino acid sequence of any one of SEQ ID NOs: 5, 6, 7, 8, 9, 10, 11, 12, 13, 14, 15, and 16 and an HLA-A24 antigen are preferred.

In order to prepare CTLs as used in adoptive immunotherapy, for example, peripheral lymphocytes are isolated from a patient, and stimulated in vitro with a peptide of the invention (e.g. a cancer antigen peptide consisting of an amino acid sequence of any one of SEQ ID NOs: 5, 6, 7, 8, 9, 10, 11, 12, 13, 14, 15, and 16), or a polynucleotide encoding the peptide of the invention (e.g. a polynucleotide encoding the peptide comprising an amino acid sequence of any one of SEQ ID NOs: 5, 6, 7, 8, 9, 10, 11, 12, 13, 14, 15, and 16) or an expression vector comprising the same (*Journal of Experimental Medicine* 1999, 190: 1669).

The CTLs of the present invention prepared as described above are useful as an active ingredient comprised in a cancer vaccine, or in adoptive immunotherapy.

(VI) Pharmaceutical Compositions Usable as Cancer Vaccines

Peptides of the present invention, polynucleotides of the present invention, expression vectors of the present invention, antigen-presenting cells of the present invention, and CTLs of the present invention as described above may be used as an active ingredient comprised in a composition for inducing CTLs or a cancer vaccine, when formulated into a form as appropriate for those respective substances, which are illustrated below.

(6-1) Cancer Vaccines Comprising a Peptide of the Present Invention as an Active Ingredient CTLs induced by the peptides of the invention, which have an activity to induce CTLs, can destroy cancers via their cytotoxic activity and the lymphokine productions. Thus, the peptides of the present invention can be used as an active ingredient comprised in a cancer vaccine for treatment or prevention of cancers. In the embodiment, the invention provides a cancer vaccine which comprises as an effective ingredient a peptide of the invention (a pharmaceutical composition usable as cancer vaccines). When the cancer vaccine of the invention is administered to a cancer patient positive for HLA-A24 and positive for WT1, the peptide (e.g. a cancer antigen peptide consisting of an amino acid sequence of any one of SEQ ID NOs: 5, 6, 7, 8, 9, 10, 11, 12, 13, 14, 15, and 16) is presented on an HLA-A24 antigen of antigen-presenting cells, and then CTLs specific for the presented complex comprising the HLA-A24 antigen and the peptide efficiently proliferate, and destroy cancer cells. In this way, treatment or prevention of cancers is achieved. The cancer vaccines of the invention can be used to treat or present cancers wherein the expression level of the WT1 gene is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

In this connection, as another embodiment, the invention provides a method for treatment or prevention of a cancer, which comprises administering an effective amount of the cancer vaccines of the present invention to a cancer patient in need who is positive for an HLA-A24, and positive for WT1.

The cancer vaccines comprising a peptide of the present invention as an active ingredient may either comprise a single CTL epitope (e.g. a cancer antigen peptide consisting of an amino acid sequence of any one of SEQ ID NOs: 5, 6, 7, 8, 9, 10, 11, 12, 13, 14, 15, and 16) as an active ingredient, or an epitope peptide linked with another peptide (a CTL epitope or a helper epitope) as an active ingredient. Recently, it has been demonstrated that an epitope peptide wherein many CTL epitopes (antigen peptides) are linked each other has an activity to induce CTLs effectively in vivo. For example, Journal of Immunology 1998, 161: 3186-3194 describes that an about 30-mer epitope peptide wherein HLA-A2, -A3, -A11, B53-restricted CTL epitopes (antigen peptide) derived from a cancer antigen protein PSA, are linked each other induced CTLs specific for the relevant CTL epitope in vivo. Also, it has been demonstrated that an epitope peptide wherein a CTL epitope and a helper epitope are linked each other effectively induced CTLs. When a peptide of the invention is administered in a form of such epitope peptides, the peptide is introduced into antigen-presenting cells, and then subject to intracellular degradation to generate respective antigen peptides, which bind an HLA antigen to form complexes. The complexes are presented compactly on the cell surface of antigen-presenting cells, and then CTLs specific for the complexes efficiently proliferate, and destroy cancer cells. In this way, treatment or prevention of cancers is achieved.

Cancer vaccines comprising the peptide of the present invention as an active ingredient may be also administered together with a pharmaceutically acceptable carrier such as a suitable adjuvant, or in a particulate dosage form in order to effectively establish the cellular immunity. For such purpose, those adjuvants described in the literature (Clin. Microbiol. Rev., 7:277-289, 1994) are applicable, and specifically include bacterium-derived components, cytokines, plant-derived components, mineral gels such as aluminium hydroxide, surfactants such as lysolecithin and Pluronic polyol, polyanions, peptides, and oil emulsions (emulsion formulations). Also, liposomal formulations, particulate formulations in which the ingredient is bound to beads having a diameter of several µm, or formulations in which the ingredient is attached to lipids are also possible.

Administration may be achieved by, for example, intradermal, subcutaneous, intramuscular or intravenous injection. Although the dose of a peptide of the present invention in the formulations may vary depending on the disease to be treated, the age and the weight of the patient, and the like, it is typical to administer 0.0001 mg to 1000 mg, preferably 0.001 mg to 1000 mg, more preferably 0.1 mg to 10 mg of a peptide of the invention every several days to every several months.

(6-2) DNA Vaccines Comprising a Polynucleotide Encoding a Peptide of the Present Invention or an Expression Vector as an Active Ingredient Not only peptides of the present invention as described above, but also a polynucleotide encoding the peptide and an expression vector comprising the polynucleotide can be used as an active ingredient in a DNA vaccine for treatment or prevention of cancers. In the embodiment, the invention provides a cancer vaccine (a pharmaceutical composition usable as cancer vaccines) which comprises as an effective ingredient a polynucleotide encoding the peptide of the invention, or an expression vector comprising the polynucleotide. In another embodiment, the invention also provides a method for treatment or prevention of a cancer, which comprises administering an effective amount of the DNA vaccine according to the invention to a patient positive for an HLA-A24, and positive for WT1.

Recently, it has been demonstrated that a polynucleotide encoding an epitope peptide wherein many CTL epitopes (antigen peptides) are linked each other or a polynucleotide encoding an epitope peptide wherein a CTL epitope and a helper epitope are linked each other has an activity to induce CTLs effectively in vivo. Journal of Immunology 1999, 162: 3915-3925, for example, describes that a DNA (minigene) encoding an epitope peptide linked with the six HLA-A2-restricted antigen peptides and the three HLA-A11-restricted antigen peptides derived from HBV, and a helper epitope has effectively induced CTLs in response to the relevant epitopes in vivo.

Thus, an appropriate expression vector that is incorporated with a polynucleotide prepared by linking one or more polynucleotides encoding the peptide of the present invention each other, or by linking the polynucleotide of the invention with a polynucleotide encoding another peptide, can be used as an active ingredient in a cancer vaccine.

Following methods may be used to allow a polynucleotide of the invention to act as an active ingredient of cancer vaccines (DNA vaccines).

Introduction of the polynucleotide of the present invention into cells may be achieved using viral vectors, or according to any one of other procedures (Nikkei-Science, April, 1994, pp. 20-45; Gekkan-Yakuji, 36(1), 23-48 (1994); Jikken-Igaku-Zokan, 12(15), 1994, and the references cited therein).

Examples of the methods using viral vectors include methods in which a DNA of the present invention is incorporated into a DNA or RNA virus such as retrovirus, adenovirus, adeno-associated virus, herpesvirus, vaccinia virus, poxvirus, poliovirus, or Sindbis virus, and introduced into cells. Among these methods, those using retrovirus, adenovirus, adeno-associated virus, or vaccinia virus are particularly preferred.

Other methods include a method in which an expression plasmid is directly injected intramuscularly (DNA vaccination), liposome method, Lipofectin method, microinjection, calcium phosphate method and electroporation, and DNA vaccination and liposome method is particularly preferred.

In order to allow a polynucleotide of the present invention to act as a medicament in practice, there are an in vivo method in which the polynucleotide is directly introduced into the body, and an ex vivo method in which certain cells are obtained from human, and after introducing DNA into said cells extracorporeally, the cells are reintroduced into the body (Nikkei-Science, April, 1994, pp. 20-45; Gekkan-Yakuji, 36(1), 23-48 (1994); Jikkenn-Igaku-Zokan, 12(15), 1994; and references cited therein). An in vivo method is more preferred.

In case of in vivo methods, the DNA vaccines may be administered by any appropriate route depending on the disease and symptoms to be treated and other factors. For example, it may be administered via intravenous, intraarterial, subcutaneous, intradermal, intramuscular route, or the like. In the case of in vivo methods, the compositions may be administered in various dosage forms such as solution, and are typically formulated, for example, into the form of injection containing a polynucleotide of the present invention as an active ingredient, to which conventional carriers may also be added, if necessary. If a polynucleotide of the invention is included in liposomes or membrane-fused liposomes (such as Sendai virus (HVJ)-liposomes), the compositions may be in the form of liposome formulations such as suspension, frozen drug, centrifugally-concentrated frozen drug, or the like.

Although the dose of a polynucleotide of the invention comprised in the formulations may vary depending on the disease to be treated, the age and the weight of the patient, and the like, it is typical to administer 0.0001 mg to 100 mg, preferably 0.001 mg to 10 mg, of a polynucleotide of the invention every several days to every several months.

When the polynucleotide of the invention is administered to a cancer patient, the polypeptide corresponding to the polynucleotide is highly expressed in his or her antigen-presenting cells. Then, respective cancer antigen peptides that are generated by intracellular degradation are bound to an HLA antigen to form complexes, which complexes are presented compactly on the cell surface of antigen-presenting cells. Then, CTLs specific for the complexes efficiently proliferate, and destroy cancer cells. In this way, treatment or prevention of cancers is achieved. Cancer vaccines comprising a polynucleotide of the invention or an expression vector comprising the polynucleotide as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(6-3) Cancer Vaccines Comprising an Antigen-presenting Cell of the Present Invention as an Active Ingredient The invention provides a cancer vaccine which comprises an antigen-presenting cell of the present invention as an active ingredient.

Recently, cell therapy (DC therapy) has been reported wherein lymphocytes are isolated from the peripheral bloods of a cancer patient, and the dendritic cells induced from the lymphocytes are pulsed in vitro with a peptide or the like to prepare antigen-presenting cells, which are then returned into the patient via a subcutaneous injection or the like (*Cancer Immunol. Immunother.*, 46: 82, 1998, *J. Immunol.*, 158: p 1796, 1997, *Cancer Res.*, 59: p 1184, 1999, *Cancer Res.*, 56: p 5672, 1996, *J. Immunol.*, 161: p 5607, 1998, *J. Exp. Med.*, 184: p 465, 1996). Thus, the antigen-presenting cell of the present invention can be used as an active ingredient in a cancer vaccine in cell therapy.

The cancer vaccine which comprises the antigen-presenting cells of the invention as an active ingredient preferably contains physiological saline, phosphate buffered saline (PBS), medium, or the like to stably maintain the antigen-presenting cells. It may be administered, for example, intra-venously, subcutaneously, or intradermally. The dose is exemplified by those described in the aforementioned literatures.

By reintroducing the cancer vaccine into the body of the patient, specific CTLs are efficiently induced in patients positive for HLA-A24, and positive for WT1 so as to achieve the treatment or the prevention of the cancers. The cancer vaccine which comprises the antigen-presenting cells of the invention as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(6-4) Cancer Vaccines Comprising a CTL of the Present Invention as an Active Ingredient The invention provides a cancer vaccine which comprises as an effective ingredient a CTL of the invention (a pharmaceutical composition usable as cancer vaccines). The CTL of the invention are useful in adoptive immunotherapy hereinafter.

For melanomas, it has been observed that an adoptive immunotherapy achieves a therapeutic effect wherein tumor-infiltrating T cells isolated from the patient himself/herself are cultured ex vivo in large quantities, and then returned into the patient (*J. Natl. Cancer. Inst.*, 86:1159, 1994). Likewise, in mouse melanoma, suppression of metastasis has been observed by in vitro stimulation of splenocytes with cancer antigen peptide TRP-2, thereby proliferating CTLs specific for the cancer antigen peptide, and administering said CTLs into a melanoma-grafted mouse (*J. Exp. Med.*, 185:453, 1997). This resulted from in vitro proliferation of CTLs that specifically recognize the complex between an HLA antigen and the cancer antigen peptide on antigen-presenting cells. Accordingly, a method for treating cancers is believed to be useful, which comprises stimulating in vitro peripheral blood lymphocytes from a patient using a peptide, or a polynucleotide or an expression vector according to the present invention to proliferate tumor-specific CTLs in vitro, and subsequently returning the CTLs into the patient. Thus, the CTLs of the invention may be used as an active ingredient comprised in cancer vaccine used in adoptive immunotherapy.

A cancer vaccine which comprises the CTLs of the invention as an active ingredient preferably contains physiological saline, phosphate buffered saline (PBS), medium, or the like to stably maintain the CTLs. It may be administered, for example, intravenously, subcutaneously, or intradermally. The dose is exemplified by those described in the aforementioned literatures.

By reintroducing the cancer vaccine into the body of a patient, cytotoxic effect of CTLs on cancer cells is enhanced in a patient positive for HLA-A24 and positive for WT1, and destroys cancer cells, so as to achieve the treatment of the cancers. The cancer vaccine which comprises the CTLs of the invention as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

EXAMPLES

The present invention is further illustrated by the following examples, but is not limited by these examples in any respect.

Example 1

CTL-inducing Activities of Cysteine Residue-Substituted Type Peptides (1)

Substituted type peptides wherein the cysteine residue at position 1 of peptide A was substituted with serine residue, alanine residue, 2-aminobutyric acid residue, arginine residue, or lysine residue (peptides B, C, D, E, and F) were synthesized, and were examined for their in vivo immunogenicity, in which peptide A was a peptide wherein the methionine residue at position 2 of the peptide composed of the positions 235 to 243 of the amino acid sequence of WT1 (SEQ ID NO: 1) (WT1$_{235-243}$, SEQ ID NO: 2) was substituted with tyrosine residue. Amino acid sequences of the unsubstituted peptide, peptide A (it may be referred to as non-substituted type peptide), and the substituted type peptides, peptides B to F, are shown below:

```
                                          (SEQ ID NO: 3)
peptide A: Cys-Tyr-Thr-Trp-Asn-Gln-Met-Asn-Leu (SEQ ID NO: 5)
peptide B: Ser-Tyr-Thr-Trp-Asn-Gln-Met-Asn-Leu (SEQ ID NO: 6)
peptide C: Ala-Tyr-Thr-Trp-Asn-Gln-Met-Asn-Leu (SEQ ID NO: 7)
peptide D: Abu-Tyr-Thr-Trp-Asn-Gln-Met-Asn-Leu (SEQ ID NO: 8)
peptide E: Arg Tyr Thr Trp Asn Gln Met Asn Leu,
and
                                          (SEQ ID NO: 9)
peptide F: Lys Tyr Thr Trp Asn Gln Met Asn Leu.
```

In vivo immunogenicity of each antigen peptide was evaluated using the HLA-A2402/K$^b$ transgenic mice. The preparation of the transgenic mice and the determination of in vivo immunogenicity were conducted according to WO 02/47474, and *Int J. Cancer.* 100, 565-570 (2002) that describe them in detail.

1) Preparation and Administration of the Pharmaceutical Compositions of the Peptides The non-substituted type peptide and the substituted type peptides as described above were synthesized using Fmoc method. The peptides synthesized were each adjusted to 40 mg/ml in DMSO, and each diluted with a sterilized water to 2.4 mg/ml. They were then mixed with a 1.27 parts of Freund's incomplete adjuvant (ISA51) using a glass syringe to prepare a water-in-oil emulsion. The resultant emulsion (200 μl) was injected into the HLA-A2402/K$^b$ transgenic mouse subcutaneously in the base of the tail for immunization.

2) Preparation of Splenocytes

Seven days after the immunization, the spleen was removed and grounded on the frosted part of glass slide, and splenocytes were recovered and prepared. A portion of the splenocytes undergone hemolysis treatment with an ACK buffer (0.15 M NH$_4$Cl, 10 mM KHCO$_3$, 0.1 mM EDTA, pH 7.2-7.4) was pulsed with the above-mentioned peptide compositions at 100 μg/ml for 1 hour, and seeded into a 24-well plate at 7×10$^5$/well. Simultaneously, splenocytes not pulsed with any peptide (7×10$^6$/well) were added together, and stimulated in vitro and incubated at 37° C. for 5 to 6 days. The in vitro stimulation was carried out in RPMI1640 medium supplemented with 10% FCS, 10 mM HEPES, 20 mM L-glutamine, 1 mM sodium pyruvate, 1 mM MEM nonessential amino acids, 1% MEM vitamin and 55 μM 2-mercaptoethanol.

3) Test for Cytotoxic Activity

The test for cytotoxic activity was conducted according to the conventional manner. EL4-A2402/K$^b$ cells obtained by transforming EL-4 cells (DAINIPPON PHARMACEUTICAL CO., LTD., Catalogue No. 06-039) with an expression vector encoding HLA-A2402/K$^b$, and the EL4-A2402/K$^b$ cells pulsed with peptide A, B, C, D, E, or F were used as target cells (T). The EL4-A2402/K$^b$ cells were prepared in a similar manner to the preparation of Jurkat-A2402/K$^b$ cells described in WO 02/47474.

These cells were labeled with $^{51}$Cr (3.7 MBq/10$^6$ cells) and pulsed with the peptide at 100 μg/ml for an hour (The labeling was carried out over 2 hours, and 1 hour after the initiation of labeling, the peptide was added). Splenocytes in vitro stimulated and incubated were used as effector cells (E). They were combined with the target cells at various ratios, and $^{51}$Cr release assay (*J. Immunol.*, 1997; 159: 4753) was conducted to determine the cytotoxic activity of the effector cells. The results are shown in FIGS. 1 to 6, wherein the vertical axis shows cytotoxic activity, and the horizontal axis shows E/T ratio.

These figures show that the peptides wherein the cysteine residue at position 1 of peptide A is substituted with serine residue, alanine residue, 2-aminobutyric acid residue, arginine residue, or lysine residue, have an immunogenicity (an activity to induce CTLs) equivalent to that of the non-substituted type peptide.

Example 2

Cytotoxic Activities of Cysteine Residue-Substituted Type Peptides

Cross-reactivity of the effector cells induced by the substituted type peptides (peptides B, C, D, E, and F) to the non-substituted type peptide (peptide A) was tested. Effector cells (E) induced by immunizing the mice with peptide B, C, D, E, or F were pulsed with peptide B, C, D, E, or F, and with the non-substituted type peptide (peptide A), or EL4-A2402/K$^b$ cells not pulsed with any peptide were reacted as target cells (T), followed by that the cytotoxic activity of the effector cells was determined by $^{51}$Cr release assay. The results are shown in FIGS. 7 to 11.

The figures show that the CTLs induced by peptides B to F wherein the cysteine residue at position 1 of peptide A is substituted with serine residue, alanine residue, 2-aminobutyric acid residue, arginine residue, or lysine residue, exhibited a cross-reactivity with the non-substituted type peptide, peptide A.

Example 3

CTL-inducing Activities of Cysteine Residue-Substituted Type Peptides (2)

Substituted type peptides wherein the cysteine residue at position 1 of the natural type peptide composed of the positions 235 to 243 of WT1 (WT1$_{235-243}$, SEQ ID NO: 2) was substituted with serine residue or alanine residue (peptides G and H), and substituted type peptides wherein the cysteine residue at position 1 of peptide A (the peptide wherein the methionine residue at position 2 of WT1$_{235-243}$ is substituted with tyrosine residue, SEQ ID NO: 3) was substituted with ornithine residue or citrulline residue (peptides I and J), were synthesized, and were examined for their in vivo immunogenicity. Amino acid sequences of the substituted type peptides, peptides G to J, are shown below:

```
                                          (SEQ ID NO: 15)
peptide G: Ser Met Thr Trp Asn Gln Met Asn Leu (SEQ ID NO: 16)
peptide H: Ala Met Thr Trp Asn Gln Met Asn Leu (SEQ ID NO: 10)
peptide I: Orn Tyr Thr Trp Asn Gln Met Asn Leu (SEQ ID NO: 11)
peptide J: Cit Tyr Thr Trp Asn Gln Met Asn Leu.
```

In vivo immunogenicity was evaluated using the HLA-A2402/K$^b$ transgenic mice.

1) Preparation and Administration of the Pharmaceutical Compositions of the Peptides The substituted type peptides as described above were synthesized using Fmoc method. The peptides synthesized were each adjusted to 40 mg/ml in DMSO, and each diluted with a 10 mM phosphate buffer (pH7.5) to 2.4 mg/ml. Simultaneously, KLH (Keyhole Limpets Hemocyanin) was added to the dilutions at 0.24 mg/ml. They were then mixed with a 1.27 parts of Freund's incomplete adjuvant (ISA51) using a glass syringe to prepare a water-in-oil emulsion. The resultant emulsion (200 µl) was injected into the HLA-A2402/K$^b$ transgenic mouse subcutaneously in the base of the tail for immunization.

2) Preparation of Splenocytes

Seven days after the immunization, the spleen was removed and grounded on the frosted part of glass slide, and splenocytes were recovered and prepared. A portion of the splenocytes undergone hemolysis treatment with an ACK buffer (0.15 M NH$_4$Cl, 10 mM KHCO$_3$, 0.1 mM EDTA, pH 7.2-7.4) was pulsed with the above-mentioned peptide compositions at 100 µg/ml for 1 hour, and seeded into a 24-well plate at 7×10$^5$/well. Simultaneously, splenocytes not pulsed with any peptide (7×10$^6$/well) were added together, and stimulated in vitro and incubated at 37° C. for 5 to 6 days. The in vitro stimulation was carried out in RPMI1640 medium supplemented with 10% FCS, 10 mM HEPES, 20 mM L-glutamine, 1 mM sodium pyruvate, 1 mM MEM nonessential amino acids, 1% MEM vitamin and 55 µM 2-mercaptoethanol.

3) Test for Cytotoxic Activity

The test for cytotoxic activity was conducted according to the conventional manner. EL4-A2402/K$^b$ cells obtained by transforming EL-4 cells (DAINIPPON PHARMACEUTICAL CO., LTD., Catalogue No. 06-039) with an expression vector encoding HLA-A2402/K$^b$, and the EL4-A2402/K$^b$ cells pulsed with peptide G, I, or J were used as target cells (T). Also, Jurkat-A2402/K$^b$ cells (WO 02/47474), and Jurkat-A2402/K$^b$ cells pulsed with peptide H were used.

These cells were labeled with $^{51}$Cr (3.7 MBq/10$^6$ cells) and pulsed with the peptide at 20 µg/ml over a half-hour. Splenocytes in vitro stimulated and incubated were used as effector cells (E). They were combined with the target cells at various ratios, and $^{51}$Cr release assay (*J. Immunol.*, 1997; 159: 4753) was conducted to determine the cytotoxic activity of the effector cells. The results are shown in FIGS. 12 to 15, wherein the vertical axis shows cytotoxic activity, and the horizontal axis shows E/T ratio. These figures show that all of peptides G, H, I and J have an immunogenicity (an activity to induce CTLs).

Example 4

CTL-inducing Activities of Cysteine Residue-Substituted Type Peptides (3)

Substituted type peptides wherein the cysteine residue at position 1 of peptide A (the peptide wherein the methionine residue at position 2 of WT1$_{235-243}$ is substituted with tyrosine residue, SEQ ID NO: 3) was substituted with leucine residue, phenylalanine residue, or asparagine residue (peptides K, L and M) were synthesized, and were examined for their in vivo immunogenicity. Amino acid sequences of the substituted type peptides, peptides K to M, are shown below:

```
                                          (SEQ ID NO: 12)
peptide K: Leu-Tyr-Thr-Trp-Asn-Gln-Met-Asn-Leu (SEQ ID NO: 13)
peptide L: Phe-Tyr-Thr-Trp-Asn-Gln-Met-Asn-Leu (SEQ ID NO: 14)
peptide M: Asn-Tyr-Thr-Trp-Asn-Gln-Met-Asn-Leu
```

In vivo immunogenicity was evaluated using the HLA-A2402/K$^b$ transgenic mice.

1) Preparation and Administration of the Pharmaceutical Compositions of the Peptides The substituted type peptides were synthesized using Fmoc method. The peptides synthesized were each adjusted to 40 mg/ml in DMSO, and each diluted with a physiological saline to 2.4 mg/ml. They were then mixed with a 1.27 parts of Freund's incomplete adjuvant (ISA51) using a glass syringe to prepare a water-in-oil emulsion. The resultant emulsion (200 µl) was injected into the HLA-A2402/K$^b$ transgenic mouse subcutaneously in the base of the tail for immunization.

2) Preparation of Splenocytes

Seven days after the immunization, the spleen was removed and grounded on the frosted part of glass slide, and splenocytes were recovered and prepared. A portion of the splenocytes undergone hemolysis treatment with an ACK buffer (0.15 M NH$_4$Cl, 10 mM KHCO$_3$, 0.1 mM EDTA, pH 7.2-7.4) was pulsed with the above-mentioned peptide compositions at 100 µg/ml for 1 hour, and seeded into a 24-well plate at 7×10$^5$/well. Simultaneously, splenocytes not pulsed with any peptide (7×10$^6$/well) were added together, and stimulated in vitro and incubated at 37° C. for 5 to 6 days. The in vitro stimulation was carried out in RPMI1640 medium supplemented with 10% FCS, 10 mM HEPES, 20 mM L-glutamine, 1 mM sodium pyruvate, 1 mM MEM nonessential amino acids, 1% MEM vitamin and 55 µM 2-mercaptoethanol.

3) Test for Cytotoxic Activity

The test for cytotoxic activity was conducted according to the conventional manner. EL4-A2402/K$^b$ cells obtained by transforming EL-4 cells with an expression vector encoding HLA-A2402/K$^b$, and the EL4-A2402/K$^b$ cells pulsed with peptide K, L, or M were used as target cells (T).

Figure 16:
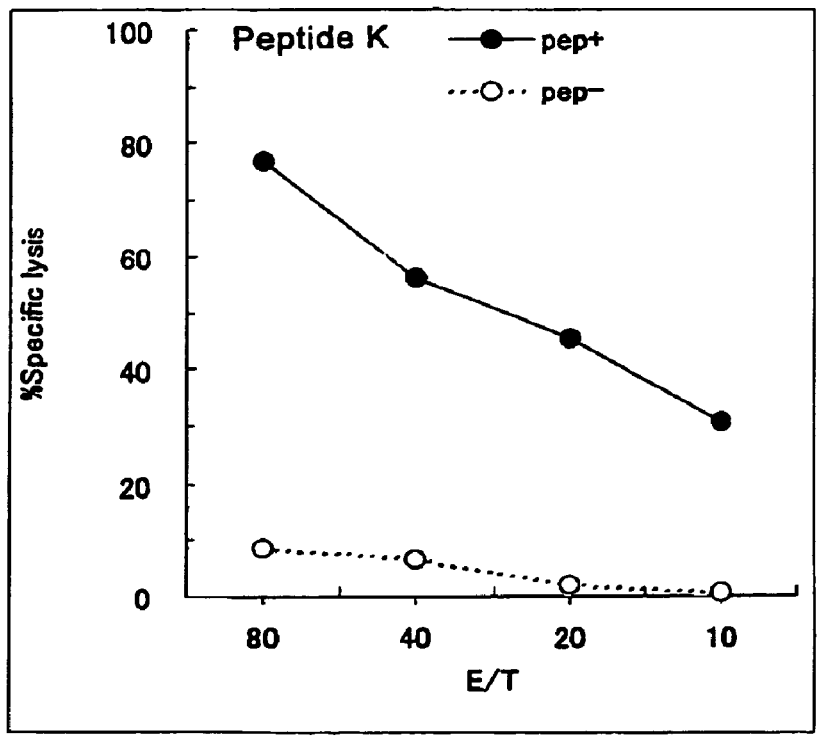
FIG. 16 is a graph showing that specific CTLs were induced when an HLA-A24-expressing transgenic mouse was immunized with peptide K wherein the cysteine residue at position 1 in peptide A is substituted with a leucine residue. In the figure, the vertical axis shows cytotoxic activity (% Specific Lysis), and the horizontal axis shows E/T ratio. In the figure, the solid circle shows the results obtained using target cells pulsed with peptide K, and the open circle shows the results obtained using cells not pulsed with any peptide.
Figure 17:
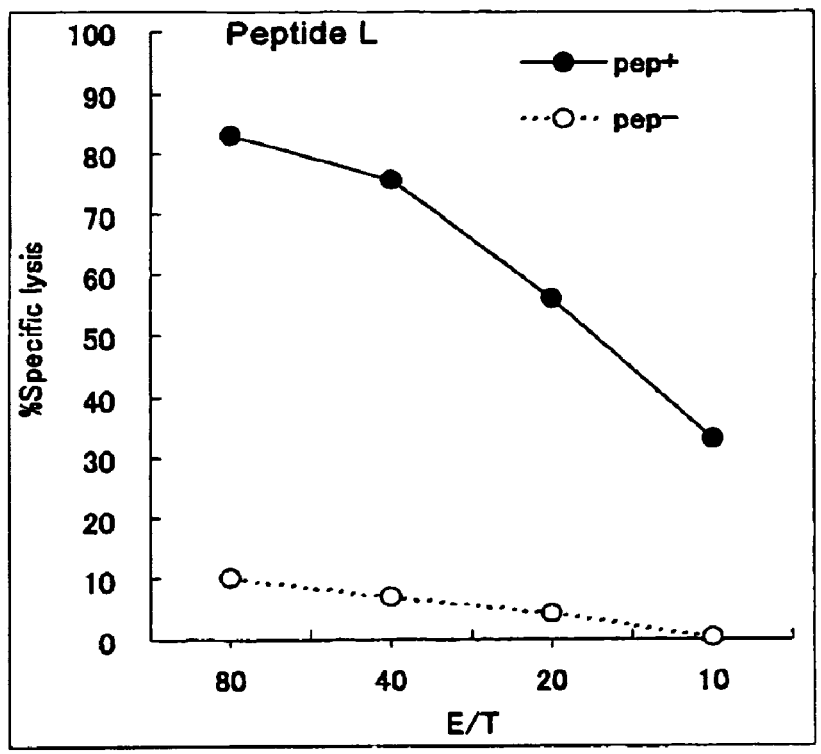
FIG. 17 is a graph showing that specific CTLs were induced when an HLA-A24-expressing transgenic mouse was immunized with peptide L wherein the cysteine residue at position 1 in peptide A is substituted with a phenylalanine residue. In the figure, the vertical axis shows cytotoxic activity (% Specific Lysis), and the horizontal axis shows E/T ratio. In the figure, the solid circle shows the results obtained using target cells pulsed with peptide L, and the open circle shows the results obtained using cells not pulsed with any peptide.
Figure 18:
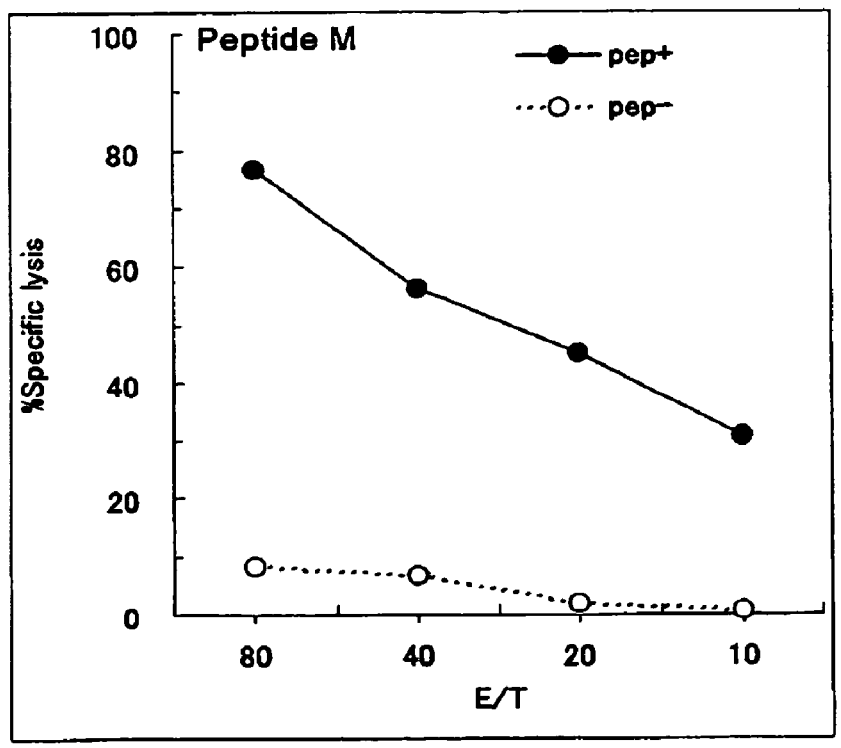
FIG. 18 is a graph showing that specific CTLs were induced when an HLA-A24-expressing transgenic mouse was immunized with peptide M wherein the cysteine residue at position 1 in peptide A is substituted with an asparagine residue. In the figure, the vertical axis shows cytotoxic activity (% Specific Lysis), and the horizontal axis shows E/T ratio. In the figure, the solid circle shows the results obtained using target cells pulsed with peptide M, and the open circle shows the results obtained using cells not pulsed with any peptide.

These cells were labeled with $^{51}$Cr (3.7 MBq/10$^6$ cells) and pulsed with the peptide at 100 μg/ml for an hour (The labeling was carried out over 2 hours, and 1 hour after the initiation of labeling, the peptide was added). Splenocytes in vitro stimulated and incubated were used as effector cells (E). They were combined with the target cells at various ratios, and $^{51}$Cr release assay (*J. Immunol.*, 1997; 159: 4753) was conducted to determine the cytotoxic activity of the effector cells. The results are shown in FIGS. 16 to 18, wherein the vertical axis shows cytotoxic activity, and the horizontal axis shows E/T ratio. These figures show that all of peptides K, L, and M have an immunogenicity (an activity to induce CTLs).

INDUSTRIAL APPLICABILITY

According to the present invention, a novel substituted type peptide of WT1 wherein the cysteine residue is substituted with a defined amino acid residue, a polynucleotide encoding said peptide, a cancer vaccine which comprises the peptide or the polynucleotide, and the like are provided. The cancer vaccine of the invention can be used to treat many cancer patients, and has advantages such as easy standardization of medical products.

Sequence Listing Free Text

The amino acid sequence of SEQ ID NO: 2 shows an synthesized peptide.

The amino acid sequence of SEQ ID NO: 3 shows an synthesized peptide.

In the amino acid sequence of SEQ ID NO: 4, the first amino acid reside Xaa is serine residue (Ser), alanine residue (Ala), 2-aminobutyric acid residue (Abu), arginine residue (Arg), lysine residue (Lys), ornithine residue (Orn), citrulline residue (Cit), leucine residue (Leu), phenylalanine residue (Phe), or asparagine residue (Asn), and the second amino acid reside Xaa is tyrosine residue (Tyr), or methionine residue (Met).

The amino acid sequence of SEQ ID NO: 5 shows an synthesized peptide.

The amino acid sequence of SEQ ID NO: 6 shows an synthesized peptide.

In the amino acid sequence of SEQ ID NO: 7, the first amino acid reside is 2-aminobutyric acid residue (Abu).

The amino acid sequence of SEQ ID NO: 8 shows an synthesized peptide.

The amino acid sequence of SEQ ID NO: 9 shows an synthesized peptide.

In the amino acid sequence of SEQ ID NO: 10, the first amino acid reside is ornithine residue (Orn).

In the amino acid sequence of SEQ ID NO: 11, the first amino acid reside is citrulline residue (Cit).

The amino acid sequence of SEQ ID NO: 12 shows an synthesized peptide.

The amino acid sequence of SEQ ID NO: 13 shows an synthesized peptide.

The amino acid sequence of SEQ ID NO: 14 shows an synthesized peptide.

The amino acid sequence of SEQ ID NO: 15 shows an synthesized peptide.

The amino acid sequence of SEQ ID NO: 16 shows an synthesized peptide.

In the amino acid sequence of SEQ ID NO: 17, the first amino acid reside is 2-aminobutyric acid residue (Abu).

The amino acid sequence of SEQ ID NO: 18 shows an synthesized peptide.

The amino acid sequence of SEQ ID NO: 19 shows an synthesized peptide.

In the amino acid sequence of SEQ ID NO: 20, the first amino acid reside is ornithine residue (Orn).

In the amino acid sequence of SEQ ID NO: 21, the first amino acid reside is citrulline residue (Cit).

The amino acid sequence of SEQ ID NO: 22 shows an synthesized peptide.

The amino acid sequence of SEQ ID NO: 23 shows an synthesized peptide.

The amino acid sequence of SEQ ID NO: 24 shows an synthesized peptide.

The amino acid sequence of SEQ ID NO: 25 shows an synthesized peptide.

The amino acid sequence of SEQ ID NO: 26 shows an synthesized peptide.

The invention claimed is:

1. An isolated peptide which comprises the amino acid sequence of the formula:

```
X-Y-Thr-Trp-Asn-Gln-Met-Asn-Leu   (SEQ ID NO: 4)
``` wherein
X represents Ala, Abu, Arg, Lys, Orn, Cit, Leu, Phe or Asn,
Y represents Tyr or Met, and
the peptide induces cytotoxic T lymphocytes (CTLs).

2. The peptide according to claim 1, which comprises

Ala-Tyr-Thr-Trp-Asn-Gln-Met-Asn-Leu (SEQ ID NO: 6),

Abu-Tyr-Thr-Trp-Asn-Gln-Met-Asn-Leu (SEQ ID NO: 7),

Arg-Tyr-Thr-Trp-Asn-Gln-Met-Asn-Leu (SEQ ID NO: 8),

Lys-Tyr-Thr-Trp-Asn-Gln-Met-Asn-Leu (SEQ ID NO: 9),

Orn-Tyr-Thr-Trp-Asn-Gln-Met-Asn-Leu (SEQ ID NO: 10),

Cit-Tyr-Thr-Trp-Asn-Gln-Met-Asn-Leu (SEQ ID NO: 11),

Leu-Tyr-Thr-Trp-Asn-Gln-Met-Asn-Leu (SEQ ID NO: 12),

Phe-Tyr-Thr-Trp-Asn-Gln-Met-Asn-Leu (SEQ ID NO: 13),

Asn-Tyr-Thr-Trp-Asn-Gln-Met-Asn-Leu (SEQ ID NO: 14), or

Ala-Met-Thr-Trp-Asn-Gln-Met-Asn-Leu (SEQ ID NO: 16).

3. The peptide according to claim 1, which consists of any one of the amino acid sequences selected from a group consisting of SEQ ID NOs: 6, 7, 8, 9, 10, 11, 12, 13, 14 and 16.

4. A pharmaceutical composition for inducing CTLs, which comprises the peptide according to claim 1 and a pharmaceutically acceptable carrier.

5. A pharmaceutical composition for inducing CTLs, which comprises the peptide according to claim 2 and a pharmaceutically acceptable carrier.

6. A pharmaceutical composition for inducing CTLs, which comprises the peptide according to claim 3 and a pharmaceutically acceptable carrier.

* * * * *